(12) United States Patent
Lippert et al.

(10) Patent No.: US 12,714,828 B2
(45) Date of Patent: Aug. 25, 2026

(54) INTRAVASCULAR GUIDEWIRE AND MICROCATHETER SYSTEM

(71) Applicant: SCIENTIA VASCULAR, INC., West Valley City, UT (US)

(72) Inventors: John A. Lippert, Park City, UT (US); Edward J. Snyder, Park City, UT (US); Clark C. Davis, Holladay, UT (US); Todd H. Turnlund, Park City, UT (US); Richard F. Maggio, Park City, UT (US)

(73) Assignee: SCIENTIA VASCULAR, INC., West Valley City, UT (US)

( * ) Notice: Subject to any disclaimer, the term of this patent is extended or adjusted under 35 U.S.C. 154(b) by 742 days.

(21) Appl. No.: 17/901,819

(22) Filed: Sep. 1, 2022

(65) Prior Publication Data

US 2023/0082226 A1 Mar. 16, 2023

Related U.S. Application Data

(60) Provisional application No. 63/271,114, filed on Oct. 22, 2021, provisional application No. 63/240,845, filed on Sep. 3, 2021.

(51) Int. Cl.

| | |
|---|---|
| ***A61M 25/01*** | (2006.01) |
| ***A61M 25/00*** | (2006.01) |
| ***A61M 25/09*** | (2006.01) |

(52) U.S. Cl.

CPC .... *A61M 25/0138* (2013.01); *A61M 25/0053* (2013.01); *A61M 25/09* (2013.01); *A61M 2025/09133* (2013.01)

(58) Field of Classification Search

CPC ...... A61M 2025/0042; A61M 25/0045; A61M 25/005; A61M 25/0053; A61M 25/0054; A61M 2025/0059; A61M 25/0138; A61M 25/0141; A61M 25/0144; A61M 25/0172; A61M 2025/0175; A61M 25/09;

(Continued)

(56) References Cited

U.S. PATENT DOCUMENTS

| | | | |
|---|---|---|---|
| 2,022,065 | A | 11/1935 | Wappler |
| 2,187,299 | A | 1/1940 | Burkhardt |

(Continued)

FOREIGN PATENT DOCUMENTS

| | | | |
|---|---|---|---|
| AU | 07230/40 | B2 | 8/2000 |
| AU | 733966 | B2 | 5/2001 |

(Continued)

OTHER PUBLICATIONS

Lauric A, et al. J NeuroIntervent Surg 2014;6:733-739. doi: 10.1136/neurintsurg-2013-010987 (Year: 2013).*

(Continued)

*Primary Examiner* — Kami A Bosworth
*Assistant Examiner* — Avery Smale
(74) *Attorney, Agent, or Firm* — Workman Nydegger

(57) ABSTRACT

Disclosed are guidewire and catheter systems that can be used to facilitate desirable catheter axial response (e.g., pushability) over a guidewire for advancement through patient vasculature. Features of the guidewire and catheter systems enable the catheter to advance over the guidewire within the tortuous paths of a patient's vasculature in response to push forces that do not exceed 50 g.

19 Claims, 19 Drawing Sheets

(58) Field of Classification Search
CPC ........... A61M 2025/09133; A61M 2025/0915; A61M 25/0051
See application file for complete search history.

(56) References Cited

U.S. PATENT DOCUMENTS 3,183,702 A 5/1965 Zittell
3,572,334 A 3/1971 Petterson
3,612,058 A 10/1971 Ackerman
3,709,271 A 1/1973 Flory
3,920,058 A 11/1975 Walker
4,163,406 A 8/1979 Crawford
4,239,069 A 12/1980 Zimmerman
4,416,312 A 11/1983 Oestberg
4,688,540 A 8/1987 Ono
4,719,924 A 1/1988 Crittenden et al.
4,801,297 A 1/1989 Mueller
4,846,186 A 7/1989 Box et al.
4,895,168 A 1/1990 Machek
4,989,608 A 2/1991 Ratner
5,047,045 A 9/1991 Arney et al.
5,069,217 A 12/1991 Fleischhacker, Jr.
5,084,022 A 1/1992 Claude
5,095,915 A 3/1992 Engelson
5,102,390 A 4/1992 Crittenden et al.
5,144,959 A 9/1992 Gambale et al.
5,147,317 A 9/1992 Shank et al.
5,154,725 A 10/1992 Leopold
5,174,302 A 12/1992 Palmer
5,315,996 A 5/1994 Lundquist
5,326,374 A 7/1994 Ilbawi et al.
5,345,945 A 9/1994 Hodgson et al.
5,366,464 A 11/1994 Belknap
5,372,587 A 12/1994 Hammerslag et al.
5,381,782 A 1/1995 Delarama et al.
5,382,259 A 1/1995 Phelps et al.
5,385,152 A 1/1995 Abele et al.
5,437,288 A 8/1995 Schwartz et al.
5,441,483 A 8/1995 Avitall
D363,544 S 10/1995 Rowland et al.
D363,776 S 10/1995 Rowland et al.
5,480,382 A 1/1996 Hammerslag et al.
5,506,682 A 4/1996 Pryor
5,507,751 A 4/1996 Goode et al.
5,551,444 A 9/1996 Finlayson
5,554,114 A 9/1996 Wallace et al.
5,569,218 A 10/1996 Berg
5,573,520 A 11/1996 Schwartz et al.
5,573,867 A 11/1996 Zafred et al.
5,606,981 A 3/1997 Tartacower et al.
5,659,205 A 8/1997 Weisser
5,673,707 A 10/1997 Chandrasekaran
5,676,659 A 10/1997 Mcgurk
5,685,568 A 11/1997 Pirrello
5,685,868 A 11/1997 Lundquist
5,690,120 A 11/1997 Jacobsen et al.
5,706,826 A 1/1998 Schwager
5,741,429 A 4/1998 Donadio et al.
5,746,701 A 5/1998 Noone
5,772,609 A 6/1998 Nguyen et al.
5,792,154 A 8/1998 Doan et al.
5,797,857 A 8/1998 Obitsu
5,800,454 A 9/1998 Jacobsen et al.
5,833,631 A 11/1998 Nguyen
5,833,632 A 11/1998 Jacobsen et al.
5,842,461 A 12/1998 Azuma
5,860,963 A 1/1999 Azam et al.
5,876,356 A 3/1999 Viera et al.
5,911,715 A 6/1999 Berg et al.
5,911,717 A 6/1999 Jacobsen et al.
5,916,194 A 6/1999 Jacobsen et al.
5,931,830 A 8/1999 Jacobsen et al.
5,954,672 A 9/1999 Schwager
6,004,279 A 12/1999 Crowley et al.
6,014,919 A 1/2000 Jacobsen
6,017,319 A 1/2000 Jacobsen et al.
6,022,343 A 2/2000 Johnson et al.
6,022,369 A 2/2000 Jacobsen et al.
6,027,526 A 2/2000 Limon et al.
6,027,863 A 2/2000 Donadio, III
6,033,288 A 3/2000 Weisshaus et al.
6,033,394 A 3/2000 Vidlund et al.
6,056,702 A 5/2000 Lorenzo
6,063,101 A 5/2000 Jacobsen et al.
6,110,164 A 8/2000 Vidlund
6,132,389 A 10/2000 Cornish et al.
6,139,510 A 10/2000 Palermo
6,139,511 A 10/2000 Huter et al.
D435,909 S 1/2001 Ogino et al.
6,168,570 B1 1/2001 Ferrera
6,179,828 B1 1/2001 Mottola et al.
6,183,410 B1 2/2001 Jacobsen et al.
6,183,420 B1 2/2001 Douk et al.
6,214,042 B1 4/2001 Jacobsen et al.
6,228,073 B1 5/2001 Noone et al.
6,245,030 B1 6/2001 Dubois et al.
6,251,086 B1 6/2001 Cornelius et al.
6,260,458 B1 7/2001 Jacobsen et al.
6,261,246 B1 7/2001 Pantages et al.
6,273,881 B1 8/2001 Kiemeneij
6,302,870 B1 10/2001 Jacobsen et al.
6,306,105 B1 10/2001 Rooney et al.
6,346,091 B1 2/2002 Jacobsen et al.
6,356,791 B1 3/2002 Westlund et al.
6,402,706 B2 6/2002 Richardson et al.
6,428,489 B1 8/2002 Jacobsen et al.
6,431,039 B1 8/2002 Jacobsen et al.
6,436,056 B1 8/2002 Wang et al.
6,440,088 B1 8/2002 Jacobsen et al.
6,458,867 B1 10/2002 Wang et al.
6,464,651 B1 10/2002 Hiejima et al.
6,492,615 B1 12/2002 Flanagan
6,494,894 B2 12/2002 Mirarchi
6,527,732 B1 3/2003 Strauss et al.
6,527,746 B1 3/2003 Oslund et al.
6,553,880 B2 4/2003 Jacobsen et al.
6,554,820 B1 4/2003 Wendlandt et al.
6,558,355 B1 5/2003 Metzger et al.
6,579,246 B2 6/2003 Jacobsen et al.
6,602,207 B1 8/2003 Mam et al.
6,606,985 B2 8/2003 Negishi
6,610,046 B1 8/2003 Usami et al.
6,627,724 B2 9/2003 Meijs et al.
6,648,874 B2 11/2003 Parisi et al.
6,652,508 B2 11/2003 Griffin et al.
6,671,560 B2 12/2003 Westlund et al.
6,766,720 B1 7/2004 Jacobsen et al.
6,805,676 B2 10/2004 Klint
6,866,642 B2 3/2005 Kellerman et al.
7,001,369 B2 2/2006 Griffin et al.
RE39,018 E 3/2006 Azuma et al.
7,024,885 B2 4/2006 Villalobos
7,097,624 B2 8/2006 Campion et al.
7,110,910 B1 9/2006 Deffenbaugh et al.
7,128,718 B2 10/2006 Hojeibane et al.
7,172,587 B2 2/2007 Poole et al.
7,182,735 B2 2/2007 Shireman et al.
7,276,062 B2 10/2007 Mcdaniel et al.
7,338,345 B2 3/2008 Fujinami
7,421,929 B2 9/2008 French
7,494,474 B2 2/2009 Richardson et al.
7,507,246 B2 3/2009 Mcguckin et al.
D598,094 S 8/2009 Alber
7,621,880 B2 11/2009 Ryan et al.
7,637,875 B2 12/2009 Yutaka
7,641,622 B2 1/2010 Satou et al.
D611,596 S 3/2010 Kousai et al.
7,670,302 B2 3/2010 Griffin et al.
7,699,792 B2 4/2010 Hofmann et al.
7,722,545 B2 5/2010 Bertsch
7,722,552 B2 5/2010 Aimi et al.
7,744,545 B2 6/2010 Aimi et al.
7,747,314 B2 6/2010 Parins et al.
7,753,859 B2 7/2010 Kinoshita et al.

(56) References Cited

U.S. PATENT DOCUMENTS 7,766,896 B2 8/2010 Kornkven et al.
7,769,839 B2 8/2010 Boivie et al.
7,785,273 B2 8/2010 Eskuri
7,789,839 B2 9/2010 Lupton
7,806,837 B2 10/2010 Rasmussen et al.
7,878,984 B2 2/2011 Jacobsen et al.
7,883,474 B1 2/2011 Mirigian et al.
7,914,467 B2 3/2011 Layman et al.
7,942,832 B2 5/2011 Kanuka et al.
7,967,762 B2 6/2011 Corl et al.
7,989,042 B2 8/2011 Obara et al.
8,007,434 B2 8/2011 Olson
8,043,314 B2 10/2011 Noriega et al.
8,048,004 B2 11/2011 Davis et al.
8,092,444 B2 1/2012 Lentz et al.
8,105,246 B2 1/2012 Voeller et al.
8,128,579 B2 3/2012 Chen et al.
8,128,580 B2 3/2012 Fujimagari et al.
8,137,293 B2 3/2012 Zhou et al.
8,167,821 B2 5/2012 Sharrow
8,257,279 B2 9/2012 Jacobsen
8,292,827 B2 10/2012 Musbach et al.
8,292,828 B2 10/2012 Uihlein
8,357,140 B2 1/2013 Majercak et al.
8,376,865 B2 2/2013 Forster et al.
8,376,961 B2 2/2013 Layman et al.
8,377,056 B2 2/2013 Oyola et al.
8,409,114 B2 4/2013 Parins
8,409,169 B1 4/2013 Moss
8,444,577 B2 5/2013 Bunch et al.
8,454,535 B2 6/2013 Majercak et al.
8,460,213 B2 6/2013 Northrop
8,465,469 B2 6/2013 Brightbill
8,468,919 B2 6/2013 Christian et al.
8,500,658 B2 8/2013 Boyle et al.
8,517,959 B2 8/2013 Kurosawa et al.
8,535,243 B2 9/2013 Shireman
8,540,648 B2 9/2013 Uihlein
8,540,668 B2 9/2013 Griffin et al.
8,551,020 B2 10/2013 Chen et al.
8,551,021 B2 10/2013 Voeller et al.
8,556,914 B2 10/2013 Vrba
8,585,643 B2 11/2013 Vo et al.
8,622,931 B2 1/2014 Teague et al.
8,622,933 B2 1/2014 Maki et al.
8,636,270 B2 1/2014 Ostrovsky
8,728,075 B2 5/2014 Wu et al.
8,758,269 B2 6/2014 Miyata et al.
8,784,337 B2 7/2014 Voeller et al.
8,795,202 B2 8/2014 Northrop et al.
8,795,254 B2 8/2014 Layman et al.
8,821,477 B2 9/2014 Northrop et al.
8,870,790 B2 10/2014 Davis et al.
8,900,163 B2 12/2014 Jacobsen et al.
8,915,865 B2 12/2014 Jacobsen et al.
8,932,235 B2 1/2015 Jacobsen et al.
8,936,558 B2 1/2015 Jacobsen et al.
8,939,916 B2 1/2015 Jacobsen et al.
8,956,310 B2 2/2015 Miyata et al.
9,011,511 B2 4/2015 Gregorich et al.
9,067,332 B2 6/2015 Lippert et al.
9,067,333 B2 6/2015 Lippert et al.
9,072,873 B2 7/2015 Lippert et al.
9,072,874 B2 7/2015 Northrop et al.
D742,000 S 10/2015 Kanazawa
9,162,040 B2 10/2015 Vo et al.
9,227,037 B2 1/2016 Northrop
9,254,143 B2 2/2016 Huynh et al.
9,364,589 B2 6/2016 Cage et al.
9,375,234 B2 6/2016 Vrba
9,433,762 B2 9/2016 Griffin et al.
9,439,557 B2 9/2016 Boulais
9,550,013 B2 1/2017 Kawasaki
9,616,195 B2 4/2017 Lippert et al.
9,623,212 B2 4/2017 Tano et al.
9,662,798 B2 5/2017 Christian et al.
9,700,702 B2 7/2017 Tano et al.
9,808,595 B2 11/2017 Turnlund et al.
9,839,764 B2 12/2017 Chouinard
9,848,882 B2 12/2017 Lippert
D809,138 S 1/2018 Khan et al.
9,950,137 B2 4/2018 Lippert et al.
9,999,748 B2 6/2018 Cajamarca et al.
10,016,210 B2 7/2018 Lenker et al.
10,028,666 B2 7/2018 Gregorich
10,052,013 B2 8/2018 Boulais
10,149,608 B2 12/2018 Fujitani
D839,426 S 1/2019 Bajwa
D847,335 S 4/2019 Kuwada
10,252,024 B2 4/2019 Northrop
D855,180 S 7/2019 Haefliger
10,350,383 B2 7/2019 Shuman
10,363,389 B2 7/2019 Lippert et al.
D855,800 S 8/2019 Gabay et al.
10,420,537 B2 9/2019 Salahieh et al.
10,441,746 B2 10/2019 Besselink
10,456,556 B2 10/2019 Cabiri
10,639,456 B2 5/2020 Peralta
10,668,258 B1 * 6/2020 Calhoun ............... A61M 29/02
10,675,057 B2 6/2020 Krieger et al.
10,675,444 B2 6/2020 Kauphusman et al.
10,758,710 B2 9/2020 Romano
10,806,893 B2 10/2020 Jaroch
10,821,268 B2 11/2020 Snyder et al.
10,835,183 B2 11/2020 Sham et al.
11,007,345 B2 5/2021 Cottone
11,052,226 B2 7/2021 Salahieh et al.
11,052,228 B2 7/2021 Lippert et al.
11,141,566 B2 10/2021 Cabiri
D946,148 S 3/2022 Takemoto
11,278,704 B2 3/2022 Pleijers
11,305,095 B2 4/2022 Snyder et al.
11,317,938 B2 5/2022 Lenker et al.
11,369,351 B2 6/2022 Davis et al.
11,471,645 B2 10/2022 Mcniven et al.
11,497,512 B2 11/2022 Wallace et al.
11,565,093 B2 1/2023 Kirt et al.
D980,427 S 3/2023 Method et al.
11,679,236 B2 6/2023 Von et al.
11,724,065 B2 8/2023 Tilson et al.
11,724,068 B2 8/2023 Von et al.
11,759,217 B2 9/2023 Keating et al.
11,766,539 B2 9/2023 Yee et al.
D1,014,751 S 2/2024 Shih
11,918,753 B2 3/2024 Moquin et al.
11,957,312 B2 4/2024 Boulais
12,178,975 B2 12/2024 Lippert et al.
2001/0009980 A1 7/2001 Richardson et al.
2001/0044624 A1 11/2001 Seraj et al.
2002/0013540 A1 1/2002 Jacobsen et al.
2002/0019599 A1 2/2002 Rooney et al.
2002/0049392 A1 4/2002 Demello
2002/0062524 A1 5/2002 Vogland et al.
2002/0078808 A1 6/2002 Jacobsen et al.
2002/0082524 A1 6/2002 Anderson et al.
2003/0009208 A1 1/2003 Snyder et al.
2003/0023190 A1 1/2003 Cox
2003/0060732 A1 3/2003 Jacobsen et al.
2003/0069521 A1 4/2003 Reynolds et al.
2003/0069522 A1 4/2003 Jacobsen et al.
2003/0093059 A1 5/2003 Griffin et al.
2003/0125641 A1 7/2003 Jafari et al.
2004/0039371 A1 2/2004 Tockman et al.
2004/0054349 A1 3/2004 Brightbill
2004/0087933 A1 5/2004 Lee et al.
2004/0093060 A1 5/2004 Seguin et al.
2004/0102719 A1 5/2004 Keith et al.
2004/0102720 A1 5/2004 Kellerman et al.
2004/0111044 A1 6/2004 Davis et al.
2004/0122340 A1 6/2004 Vrba et al.
2004/0167437 A1 8/2004 Sharrow et al.
2004/0167440 A1 8/2004 Sharrow
2004/0167443 A1 8/2004 Shireman et al.
2004/0171996 A1 9/2004 Kiemeneij

(56) References Cited

U.S. PATENT DOCUMENTS

2004/0181174 A2 9/2004 Davis et al.
2004/0186485 A1 9/2004 Kear
2004/0193140 A1 9/2004 Griffin et al.
2004/0225292 A1 11/2004 Sasso et al.
2004/0254450 A1 12/2004 Griffin et al.
2005/0054953 A1 3/2005 Ryan et al.
2005/0065456 A1 3/2005 Eskuri
2005/0124976 A1 6/2005 Devens et al.
2005/0216049 A1 9/2005 Jones et al.
2005/0274384 A1 12/2005 Tran et al.
2006/0041186 A1 2/2006 Vancaillie
2006/0074442 A1 4/2006 Noriega et al.
2006/0089618 A1 4/2006 Mcferran et al.
2006/0112802 A1 6/2006 Fujinami
2006/0121218 A1 6/2006 Obara et al.
2006/0189896 A1* 8/2006 Davis ................ A61M 25/0054 600/585
2006/0241519 A1 10/2006 Hojeibane et al.
2006/0247661 A1 11/2006 Richards et al.
2006/0262474 A1 11/2006 Chen et al.
2006/0264904 A1 11/2006 Kerby et al.
2007/0010786 A1 1/2007 Casey et al.
2007/0055302 A1 3/2007 Henry et al.
2007/0083132 A1 4/2007 Sharrow
2007/0100285 A1 5/2007 Griffin et al.
2007/0112331 A1 5/2007 Weber et al.
2007/0135763 A1 6/2007 Musbach et al.
2007/0142893 A1 6/2007 Buiser et al.
2007/0167876 A1 7/2007 Euteneuer et al.
2007/0185415 A1 8/2007 Ressemann et al.
2007/0208405 A1 9/2007 Goodin et al.
2007/0213689 A1 9/2007 Grewe et al.
2007/0221230 A1 9/2007 Thompson et al.
2007/0233039 A1 10/2007 Mitelberg
2007/0250036 A1 10/2007 Volk et al.
2007/0287955 A1 12/2007 Layman et al.
2008/0021347 A1 1/2008 Jacobsen et al.
2008/0021401 A1 1/2008 Jacobsen et al.
2008/0021404 A1 1/2008 Jacobsen et al.
2008/0021406 A1 1/2008 Jacobsen et al.
2008/0033421 A1 2/2008 Davis et al.
2008/0064989 A1 3/2008 Chen et al.
2008/0077049 A1 3/2008 Hirshman
2008/0086854 A1 4/2008 Boyd et al.
2008/0097246 A1 4/2008 Stafford
2008/0097247 A1 4/2008 Eskuri
2008/0097248 A1 4/2008 Munoz et al.
2008/0119869 A1 5/2008 Teague et al.
2008/0122226 A1 5/2008 Madison
2008/0125674 A1 5/2008 Bilecen et al.
2008/0140101 A1 6/2008 Carley et al.
2008/0147170 A1 6/2008 Vrba
2008/0188298 A1 8/2008 Seelig et al.
2008/0188928 A1 8/2008 Salahieh et al.
2008/0200839 A1 8/2008 Bunch et al.
2008/0262474 A1 10/2008 Northrop
2008/0269641 A1 10/2008 O'Shaughnessy et al.
2008/0319525 A1 12/2008 Tieu et al.
2009/0036832 A1 2/2009 Skujins et al.
2009/0036833 A1 2/2009 Parins
2009/0043283 A1 2/2009 Turnlund et al.
2009/0043372 A1 2/2009 Northrop et al.
2009/0043483 A1 2/2009 Abe et al.
2009/0118675 A1 5/2009 Czyscon et al.
2009/0118704 A1 5/2009 Sharrow et al.
2009/0163945 A1 6/2009 Richard et al.
2009/0177119 A1 7/2009 Heidner et al.
2009/0177185 A1 7/2009 Northrop
2009/0254000 A1 10/2009 Layman et al.
2009/0292225 A1 11/2009 Chen et al.
2009/0318892 A1 12/2009 Aboytes et al.
2010/0063479 A1 3/2010 Merdan et al.
2010/0069882 A1 3/2010 Jennings et al.
2010/0114017 A1 5/2010 Lenker et al.
2010/0114302 A1 5/2010 Tzafriri et al.
2010/0139465 A1 6/2010 Christian et al.
2010/0145308 A1 6/2010 Layman et al.
2010/0228150 A1 9/2010 Zimmerman et al.
2010/0256527 A1 10/2010 Lippert et al.
2010/0256528 A1 10/2010 Lippert et al.
2010/0256601 A1 10/2010 Lippert et al.
2010/0256602 A1 10/2010 Lippert et al.
2010/0256603 A1 10/2010 Lippert et al.
2010/0256604 A1 10/2010 Lippert et al.
2010/0256605 A1 10/2010 Lippert et al.
2010/0256606 A1 10/2010 Lippert et al.
2010/0318066 A1 12/2010 Miyata et al.
2011/0011226 A1 1/2011 Tsurusawa et al.
2011/0022003 A1 1/2011 Tekulve
2011/0160680 A1 6/2011 Cage et al.
2011/0245807 A1 10/2011 Sakata et al.
2011/0245808 A1 10/2011 Voeller et al.
2011/0251519 A1 10/2011 Romoscanu
2011/0313417 A1 12/2011 De et al.
2012/0046575 A1 2/2012 Brown
2012/0065623 A1 3/2012 Nelson et al.
2012/0158034 A1 6/2012 Wilson et al.
2012/0209073 A1 8/2012 Mcweeney et al.
2012/0239074 A1 9/2012 Aboytes et al.
2012/0271397 A1 10/2012 Muzslay et al.
2012/0289938 A1 11/2012 Northrop et al.
2013/0018359 A1 1/2013 Coyle
2013/0096553 A1 4/2013 Hill et al.
2013/0110000 A1 5/2013 Tully et al.
2013/0131642 A1 5/2013 Miyata et al.
2013/0144267 A1 6/2013 Chan et al.
2013/0184703 A1 7/2013 Shireman et al.
2013/0226033 A1 8/2013 Eskuri
2013/0255456 A1 10/2013 Christian et al.
2013/0274784 A1 10/2013 Lenker et al.
2014/0012281 A1 1/2014 Wang et al.
2014/0031719 A1 1/2014 Kanazawa
2014/0058324 A1 2/2014 Salahieh et al.
2014/0094787 A1 4/2014 Reynolds
2014/0187983 A1 7/2014 Anderson
2014/0257363 A1 9/2014 Lippert
2014/0276109 A1 9/2014 Gregorich
2014/0276117 A1 9/2014 Burkett
2014/0276787 A1 9/2014 Wang et al.
2014/0279109 A1 9/2014 Vasquez et al.
2014/0309657 A1 10/2014 Ben-Ami
2014/0336620 A1 11/2014 Layman et al.
2014/0343538 A1 11/2014 Lenker et al.
2015/0011834 A1 1/2015 Ayala et al.
2015/0011964 A1 1/2015 Abner et al.
2015/0057639 A1 2/2015 Storbeck et al.
2015/0190614 A1 7/2015 Uihlein
2015/0190615 A1 7/2015 Shaltis
2015/0216533 A1 8/2015 Gray et al.
2015/0238734 A1 8/2015 Kanazawa
2015/0290432 A1 10/2015 Mathews et al.
2015/0297863 A1 10/2015 Hannon et al.
2015/0305710 A1 10/2015 Stigall et al.
2015/0306355 A1 10/2015 Idstrom
2016/0001048 A1 1/2016 Koike
2016/0008585 A1 1/2016 Tano
2016/0045101 A1 2/2016 Nakatate et al.
2016/0058382 A1 3/2016 Burkett et al.
2016/0089128 A1 3/2016 Weber et al.
2016/0113793 A1 4/2016 Nishigishi
2016/0135827 A1 5/2016 Elsesser et al.
2016/0199620 A1 7/2016 Pokorney et al.
2016/0235337 A1 8/2016 Govari et al.
2016/0287054 A1 10/2016 Fujitani
2016/0310702 A1 10/2016 Cabiri
2016/0361520 A1 12/2016 Braun
2016/0367788 A1 12/2016 Jimenez et al.
2016/0375226 A1 12/2016 Nabeshima et al.
2017/0047740 A1 2/2017 Narla
2017/0049594 A1 2/2017 Banas et al.
2017/0136213 A1 5/2017 Kauphusman et al.
2017/0189643 A1 7/2017 Christian et al.
2017/0203076 A1 7/2017 Groneberg et al.
2017/0215954 A1 8/2017 Datta et al.

(56) References Cited

U.S. PATENT DOCUMENTS

2017/0234411 A1 8/2017 Dewaele et al.
2017/0281909 A1 10/2017 Northrop et al.
2018/0015260 A1 1/2018 Sano et al.
2018/0015261 A1 1/2018 Lippert et al.
2018/0015262 A1 1/2018 Lippert et al.
2018/0015263 A1 1/2018 Lippert et al.
2018/0028177 A1 2/2018 Van et al.
2018/0071496 A1 3/2018 Snyder et al.
2018/0177517 A1 6/2018 Lippert et al.
2018/0185619 A1 7/2018 Batman et al.
2018/0193603 A1 7/2018 Falb et al.
2018/0193607 A1 7/2018 Lippert et al.
2018/0207407 A1 7/2018 Tanigaki
2019/0008639 A1 1/2019 Landon et al.
2019/0060612 A1 2/2019 Besselink
2019/0105463 A1 4/2019 Christian et al.
2019/0175869 A1 6/2019 Kirt et al.
2019/0247621 A1 8/2019 Romano
2019/0255290 A1* 8/2019 Snyder .............. A61M 25/0054
2019/0290883 A1 9/2019 Lippert et al.
2019/0358434 A1 11/2019 Fuller et al.
2020/0016378 A1 1/2020 Williams et al.
2020/0054860 A1 2/2020 Mcelhaney et al.
2020/0094027 A1 3/2020 Davis
2020/0121308 A1 4/2020 Davis et al.
2020/0222666 A1 7/2020 Chan et al.
2020/0222672 A1 7/2020 Davis et al.
2020/0330734 A1 10/2020 Sugita et al.
2020/0345975 A1 11/2020 Snyder
2021/0008351 A1 1/2021 Snyder et al.
2021/0022748 A1 1/2021 Lorenzo
2021/0162184 A1 6/2021 Lippert et al.
2021/0178128 A1 6/2021 Lippert et al.
2021/0213241 A1 7/2021 Christian et al.
2021/0228845 A1 7/2021 Lippert et al.
2021/0283372 A1 9/2021 Murphy
2021/0283380 A1 9/2021 Lippert et al.
2021/0307766 A1 10/2021 Keating et al.
2021/0346656 A1 11/2021 Lippert et al.
2022/0039644 A1 2/2022 Dayton et al.
2022/0047845 A1 2/2022 Niederhauser et al.
2022/0105312 A1 4/2022 Davis
2022/0105318 A1 4/2022 Davis et al.
2022/0118225 A1 4/2022 Snyder et al.
2022/0176075 A1 6/2022 Mcdermott et al.
2022/0211981 A1 7/2022 Darbellay et al.
2022/0218358 A1 7/2022 Dagan et al.
2022/0273474 A1 9/2022 Koop et al.
2022/0280147 A1 9/2022 Davis
2022/0296850 A1 9/2022 Lippert
2022/0323166 A1 10/2022 Tilson et al.
2022/0378459 A1 12/2022 Lippert
2023/0010697 A1 1/2023 Sharma et al.
2023/0069698 A1 3/2023 Hallauer et al.
2023/0071512 A1 3/2023 Maggio et al.
2023/0285720 A1 9/2023 Isogai
2023/0405276 A1 12/2023 Cabiri
2024/0123196 A1 4/2024 Lippert et al.
2024/0198059 A1 6/2024 Lippert et al.
2024/0299710 A1 9/2024 Davis et al.
2025/0090813 A1 3/2025 Lippert et al.
2025/0288781 A1 9/2025 Lippert et al.

FOREIGN PATENT DOCUMENTS

AU 07745/59 B2 7/2004
AU 2008229892 A1 10/2008
BR 9709363 A 1/2000
BR 9712829 A 1/2000
CA 2255781 A1 11/1997
CA 2266685 A1 3/1998
CA 2395149 A1 6/2001
CN 1230914 A 10/1999
CN 1324285 A 11/2001
CN 1422673 A 6/2003
CN 1518428 A 8/2004
CN 1781684 A 6/2006
CN 1897892 A 1/2007
CN 101001660 A 7/2007
CN 101209365 A 7/2008
CN 101304778 A 11/2008
CN 201239164 Y 5/2009
CN 101815553 A 8/2010
CN 102049085 A 5/2011
CN 102107041 A 6/2011
CN 102438691 A 5/2012
CN 102548603 A 7/2012
CN 102824681 A 12/2012
CN 102847225 A 1/2013
CN 103301553 A 9/2013
CN 103566457 A 2/2014
CN 103764012 A 4/2014
CN 103799980 A 5/2014
CN 103860265 A 6/2014
CN 104271035 A 1/2015
CN 104302345 A 1/2015
CN 104427950 A 3/2015
CN 104602616 A 5/2015
CN 104602718 A 5/2015
CN 104619247 A 5/2015
CN 104759022 A 7/2015
CN 104812420 A 7/2015
CN 105209102 A 12/2015
CN 105228536 A 1/2016
CN 105361918 A 3/2016
CN 105545375 A 5/2016
CN 105582611 A 5/2016
CN 105682725 A 6/2016
CN 105682729 A 6/2016
CN 105828690 A 8/2016
CN 105979880 A 9/2016
CN 106455910 A 2/2017
CN 107206216 A 9/2017
CN 109715245 A 5/2019
CN 109789296 A 5/2019
CN 110691626 A 1/2020
DE 60036882 T2 7/2008
DE 69738235 T2 7/2008
EP 0521595 A2 1/1993
EP 0921754 A1 6/1999
EP 0998323 A1 5/2000
EP 0934141 B1 11/2005
EP 1239901 B1 10/2007
EP 1940498 A1 7/2008
EP 2964305 A2 1/2016
EP 2414022 B1 8/2017
EP 3866902 A1 8/2021
ES 2293660 T3 3/2008
GB 2478988 A 9/2011
JP 59-102509 A 6/1984
JP 06-154335 A 6/1994
JP 07-008560 A 1/1995
JP 08-215313 A 8/1996
JP 08-243168 A 9/1996
JP 08-243169 A 9/1996
JP 08-308934 A 11/1996
JP 11-294497 A 10/1999
JP 2000-503225 A 3/2000
JP 2000-116787 A 4/2000
JP 2000-126301 A 5/2000
JP 2000-511094 A 8/2000
JP 2000-343313 A 12/2000
JP 2001-500808 A 1/2001
JP 2002-543896 A 12/2002
JP 2003-011117 A 1/2003
JP 2004-025340 A 1/2004
JP 2004-136121 A 5/2004
JP 2004-329552 A 11/2004
JP 2004-535233 A 11/2004
JP 2005-514115 A 5/2005
JP 2005-533594 A 11/2005
JP 2005-534407 A 11/2005
JP 2007-514458 A 6/2007
JP 2007-313638 A 12/2007

(56) References Cited

FOREIGN PATENT DOCUMENTS

| | | | |
|---|---|---|---|
| JP | 2008-178656 | A | 8/2008 |
| JP | 2008-536639 | A | 9/2008 |
| JP | 2009-511184 | A | 3/2009 |
| JP | 2010-029736 | A | 2/2010 |
| JP | 2010-503484 | A | 2/2010 |
| JP | 2010-535583 | A | 11/2010 |
| JP | 2010-535588 | A | 11/2010 |
| JP | 2011-206175 | A | 10/2011 |
| JP | 4805208 | B2 | 11/2011 |
| JP | 4845313 | B2 | 12/2011 |
| JP | 2012-502743 | A | 2/2012 |
| JP | 2013-106854 | A | 6/2013 |
| JP | 2013-523282 | A | 6/2013 |
| JP | 2013-176560 | A | 9/2013 |
| JP | 2014-023727 | A | 2/2014 |
| JP | 2015-073861 | A | 4/2015 |
| JP | 2015-181723 | A | 10/2015 |
| JP | 2015-186427 | A | 10/2015 |
| JP | 2016-013269 | A | 1/2016 |
| JP | 2017-169253 | A | 9/2017 |
| KR | 2000-0015896 | A | 3/2000 |
| KR | 10-2000-0036139 | A | 6/2000 |
| NL | 2017570 | B1 | 4/2018 |
| RU | 91674 | U1 | 2/2010 |
| TW | 412468 | B | 11/2000 |
| WO | 94/06503 | A1 | 3/1994 |
| WO | 94/19039 | A1 | 9/1994 |
| WO | 95/24237 | A2 | 9/1995 |
| WO | 97/25914 | A1 | 7/1997 |
| WO | 97/43949 | A1 | 11/1997 |
| WO | 98/55173 | A1 | 12/1998 |
| WO | 98/58697 | A1 | 12/1998 |
| WO | 99/04847 | A1 | 2/1999 |
| WO | 99/53824 | A2 | 10/1999 |
| WO | 2004/011076 | A2 | 2/2004 |
| WO | 2006/025931 | A1 | 3/2006 |
| WO | 2006/058234 | A2 | 6/2006 |
| WO | 2006/113863 | A2 | 10/2006 |
| WO | 2007/050718 | A1 | 5/2007 |
| WO | 2008/034010 | A2 | 3/2008 |
| WO | 2009/020691 | A2 | 2/2009 |
| WO | 2009/020836 | A1 | 2/2009 |
| WO | 2009/020961 | A1 | 2/2009 |
| WO | 2009/020962 | A1 | 2/2009 |
| WO | 2009/058705 | A2 | 5/2009 |
| WO | 2009/143160 | A1 | 11/2009 |
| WO | 2010/077692 | A2 | 7/2010 |
| WO | 2010/115163 | A1 | 10/2010 |
| WO | 2011/123689 | A1 | 10/2011 |
| WO | 2014/005095 | A1 | 1/2014 |
| WO | 2014/066104 | A1 | 5/2014 |
| WO | 2014/077881 | A1 | 5/2014 |
| WO | 2014/138580 | A2 | 9/2014 |
| WO | 2016/047499 | A1 | 3/2016 |
| WO | 2016/117238 | A1 | 7/2016 |
| WO | 2016/136609 | A1 | 9/2016 |
| WO | 2016/152194 | A1 | 9/2016 |
| WO | 2016/158671 | A1 | 10/2016 |
| WO | 2017/151292 | A1 | 9/2017 |
| WO | 2018/017349 | A1 | 1/2018 |
| WO | 2018/017351 | A1 | 1/2018 |
| WO | 2018/218216 | A1 | 11/2018 |
| WO | 2020/150398 | A1 | 7/2020 |
| WO | 2020/217171 | A1 | 10/2020 |
| WO | 2021/150920 | A1 | 7/2021 |
| WO | 2022/159139 | A1 | 7/2022 |

OTHER PUBLICATIONS

Baz, R.A.; Scheau, C.; Niscoveanu, C.; Bordei, P.Morphometry of the Entire Internal Carotid Artery on CT Angiography. Medicina 2021, 57, 832. https://doi.org/10.3390/medicina57080832 (Year: 2021).*

Final Office Action received for U.S. Appl. No. 17/036,302, mailed on Jul. 30, 2024, 17 pages.

Final Office Action received for U.S. Appl. No. 17/382,271, mailed on Sep. 16, 2024, 9 pages.

Final Office Action received for U.S. Appl. No. 17/836,863, mailed on Jun. 25, 2024, 6 pages.

Non-Final Office Action received for U.S. Appl. No. 17/382,271, mailed on May 14, 2024, 22 pages.

Non-Final Office Action received for U.S. Appl. No. 17/493,265, mailed on Jun. 11, 2024, 19 pages.

Non-Final Office Action received for U.S. Appl. No. 17/752,600, mailed on Sep. 10, 2024, 11 pages.

Non-Final Office Action received for U.S. Appl. No. 18/661,472, mailed on Dec. 6, 2024, 20 pages.

Requirement for Restriction/Election received for U.S. Appl. No. 18/589,282, mailed on Dec. 30, 2024, 5 pages.

Chinese Search Report for Chinese Application No. 201780070242.X, dated Sep. 14, 2016, 4 pages.

International Search Report and Written Opinion received for PCT Patent Application No. PCT/US22/42514, mailed on Dec. 28, 2022, 11 pages.

International Search Report and Written Opinion received for PCT Patent Application No. PCT/US22/42517, mailed on Feb. 7, 2023, 11 pages.

International Search Report and Written Opinion received for PCT Patent Application No. PCT/US2021/053647, mailed on Dec. 28, 2021, 9 pages.

International Search Report and Written Opinion received for PCT Patent Application No. PCT/US21/042753, mailed on Nov. 5, 2021, 14 pages.

International Search Report and Written Opinion received for PCT Patent Application No. PCT/US21/14656, mailed on Apr. 28, 2021, 8 pages.

International Search Report and Written Opinion, PCT App. No. PCT/US2020/013754, mailed on Jun. 9, 2020, 11 pages.

European Search Report received for EP Patent Application No. 21878402, mailed on Aug. 14, 2024, 13 pages.

Intention to grant received for European Patent Application No. 23188821.5, mailed on Aug. 14, 2024, 6 pages.

Final Office Action received for U.S. Appl. No. 12/753,831, mailed on May 31, 2012.

Final Office Action received for U.S. Appl. No. 12/753,836 mailed on Feb. 17, 2016.

Final Office Action received for U.S. Appl. No. 16/855,366, mailed on Dec. 8, 2022, 18 pages.

Final Office Action received for U.S. Appl. No. 16/212,425, mailed on Aug. 3, 2020, 14 pages.

Final Office Action received for U.S. Appl. No. 12/753,831, mailed on Aug. 29, 2014.

Final Office Action received for U.S. Appl. No. 12/753,836, mailed on Jan. 9, 2015.

Final Office Action received for U.S. Appl. No. 12/753,836, mailed on Jul. 14, 2017.

Final Office Action received for U.S. Appl. No. 12/753,836, mailed on May 1, 2012.

Final Office Action received for U.S. Appl. No. 12/753,839, mailed on May 31, 2012.

Final Office Action received for U.S. Appl. No. 12/753,842, mailed on Jan. 9, 2013.

Final Office Action received for U.S. Appl. No. 12/753,842, mailed on Sep. 4, 2014.

Final Office Action received for U.S. Appl. No. 12/753,849, mailed on Jun. 6, 2012.

Final Office Action received for U.S. Appl. No. 12/753,849, mailed on Oct. 9, 2013.

Final Office Action received for U.S. Appl. No. 12/753,855, mailed on Apr. 18, 2012.

Final Office Action received for U.S. Appl. No. 12/753,855, mailed on Jan. 13, 2015.

Final Office Action received for U.S. Appl. No. 12/753,858, mailed on Jan. 17, 2014.

Final Office Action received for U.S. Appl. No. 12/753,858, mailed on Jul. 18, 2012.

(56) References Cited

OTHER PUBLICATIONS

Final Office Action received for U.S. Appl. No. 12/753,858, mailed on May 28, 2015.
Final Office Action received for U.S. Appl. No. 12/753,858, mailed on Nov. 14, 2018.
Final Office Action received for U.S. Appl. No. 12/753,858, mailed on Oct. 19, 2011.
Final Office Action received for U.S. Appl. No. 12/753,858, mailed on Oct. 20, 2017.
Final Office Action received for U.S. Appl. No. 15/606,607, mailed on Nov. 19, 2019.
Final Office Action received for U.S. Appl. No. 15/611,344, mailed on Nov. 12, 2019.
Final Office Action received for U.S. Appl. No. 15/848,878, mailed on Aug. 27, 2020, 13 pages.
Final Office Action received for U.S. Appl. No. 15/848,878, mailed on Sep. 22, 2021, 12 pages.
Final Office Action received for U.S. Appl. No. 16/281,046, mailed on May 11, 2021, 18 pages.
Final Office Action received for U.S. Appl. No. 16/616,220, mailed on Oct. 12, 2022, 17 pages.
Final Office Action received for U.S. Appl. No. 16/742,211, mailed on Mar. 14, 2023, 22 pages.
Final Office Action received for U.S. Appl. No. 17/216,127, mailed on Jun. 13, 2022, 8 pages.
Final Office Action received for U.S. Appl. No. 14/199,675, mailed on May 18, 2017.
Final Office Action received for U.S. Appl. No. 15/611,328, mailed on Sep. 24, 2019.
Final Office Action received for U.S. Appl. No. 15/698,553, mailed on Nov. 27, 2019.
Final Rejection received for U.S. Appl. No. 15/606,607, mailed on Dec. 15, 2020, 24 pages.
International Search Report and Written Opinion for application No. PCT/US17/41305 dated Oct. 2, 2017.
International Search Report and Written Opinion for Application PCT/US2017/050602 mailed on Nov. 7, 2017.
International Search Report and Written Opinion for PCT/US2009/067217 dated Dec. 16, 2010.
International Search Report and Written Opinion for PCT/US2010/029867 dated Jun. 1, 2010.
International Search Report and Written Opinion for PCT/US2014/021742 dated Aug. 27, 2014.
International Search Report and Written Opinion for PCT/US2017/041299 mailed on Oct. 2, 2017.
International Search Report and Written Opinion for PCT/US2017/041301 mailed on Oct. 2, 2017.
International Search Report and Written Opinion for PCT/US2017/068056 mailed on Feb. 26, 2018.
International Search Report and Written Opinion for PCT/US2018/034756 mailed on Aug. 14, 2018.
International Search Report and Written Opinion for PCT/US2019/019046, mailed on May 17, 2019.
International Search Report and Written Opinion for PCT/US2019/021031 mailed on Jun. 18, 2019.
International Search Report and Written Opinion received for PCT Patent Application No. PCT/US2018/034723, mailed on Sep. 5, 2018, 10 pages.
International Search Report and Written Opinion received for PCT Patent Application No. PCT/US2020/030589, mailed on Jul. 17, 2020, 7 pages.
International Search Report and Written Opinion received for PCT Patent Application No. PCT/US2021/053652, mailed on Dec. 28, 2021, 9 pages.
InternationalSearch Report and Written Opinion for application PCT/US2017/050802 mailed on Nov. 7, 2017.
Non-Final Office Action received for U.S. Appl. No. 15/606,607, mailed on Jun. 10, 2020, 26 pages.
Non-Final Office Action received for U.S. Appl. No. 15/611,328, mailed on Jun. 29, 2020, 13 pages.
Non-Final Office Action received for U.S. Appl. No. 15/848,878, mailed on Jun. 3, 2021, 13 pages.
Non-Final Office Action received for U.S. Appl. No. 15/917,255, mailed on Aug. 17, 2020, 12 pages.
Non-Final Office Action received for U.S. Appl. No. 16/281,046, mailed on Oct. 29, 2020, 18 pages.
Non-Final Office Action received for U.S. Appl. No. 16/616,139, mailed on Oct. 26, 2021, 11 pages.
Non-Final Office Action received for U.S. Appl. No. 16/616,220, mailed on Jun. 3, 2022, 20 pages.
Non-Final Office Action received for U.S. Appl. No. 16/742,211, mailed on Aug. 15, 2022, 20 pages.
Non-Final Office Action received for U.S. Appl. No. 16/855,366, mailed on Jul. 11, 2022, 13 pages.
Non-Final Office Action received for U.S. Appl. No. 16/855,366, mailed on Jun. 23, 2021, 15 pages.
Non-Final Office Action received for U.S. Appl. No. 17/036,302, mailed on Mar. 1, 2023, 29 pages.
Non-Final Office Action received for U.S. Appl. No. 17/177,782, mailed on Jan. 23, 2023, 14 pages.
Non-Final Office Action received for U.S. Appl. No. 17/177,782, mailed on Nov. 4, 2022, 7 pages.
Notice of Allowance received for U.S. Appl. No. 16/212,425, mailed on Dec. 23, 2020, 12 pages.
Notice of Allowance received for U.S. Appl. No. 16/212,425, mailed on Jan. 25, 2021, 2 pages.
Office Action received for U.S. Appl. No. 12/633,727, mailed on Oct. 16, 2012.
Office Action received for U.S. Appl. No. 12/753,831, mailed on Feb. 1, 2012.
Office Action received for U.S. Appl. No. 12/753,831, mailed on Mar. 21, 2014.
Office Action received for U.S. Appl. No. 12/753,836, mailed on Dec. 9, 2011.
Office Action received for U.S. Appl. No. 12/753,836, mailed on Dec. 23, 2016.
Office Action received for U.S. Appl. No. 12/753,836, mailed on Jul. 31, 2014.
Office Action received for U.S. Appl. No. 12/753,836, mailed on Jun. 26, 2015.
Office Action received for U.S. Appl. No. 12/753,839, mailed on Feb. 7, 2012.
Office Action received for U.S. Appl. No. 12/753,839, mailed on May 5, 2014.
Office Action received for U.S. Appl. No. 12/753,842, mailed on Aug. 1, 2012.
Office Action received for U.S. Appl. No. 12/753,842, mailed on Jan. 29, 2014.
Office Action received for U.S. Appl. No. 12/753,849, mailed on Jan. 3, 2013.
Office Action received for U.S. Appl. No. 12/753,849, mailed on May 10, 2011.
Office Action received for U.S. Appl. No. 12/753,849, mailed on May 27, 2014.
Office Action received for U.S. Appl. No. 12/753,849, mailed on Oct. 18, 2011.
Office Action received for U.S. Appl. No. 12/753,855, mailed on Feb. 28, 2014.
Office Action received for U.S. Appl. No. 12/753,855, mailed on May 21, 2015.
Office Action received for U.S. Appl. No. 12/753,855, mailed on Sep. 15, 2011.
Office Action received for U.S. Appl. No. 12/753,858, mailed on Dec. 30, 2015.
Office Action received for U.S. Appl. No. 12/753,858, mailed on Feb. 3, 2012.
Office Action received for U.S. Appl. No. 12/753,858, mailed on Mar. 13, 2018.
Office Action received for U.S. Appl. No. 12/753,858, mailed on Mar. 27, 2017.
Office Action received for U.S. Appl. No. 12/753,858, mailed on Mar. 29, 2013.

(56) References Cited

OTHER PUBLICATIONS

Office Action received for U.S. Appl. No. 12/753,858, mailed on May 10, 2011.
Office Action received for U.S. Appl. No. 12/753,858, mailed on Oct. 24, 2016.
Office Action received for U.S. Appl. No. 12/753,858, mailed on Sep. 4, 2014.
Office Action received for U.S. Appl. No. 13/901,375, mailed on Dec. 10, 2015.
Office Action received for U.S. Appl. No. 15/465,399, mailed on Apr. 23, 2018.
Office Action received for U.S. Appl. No. 15/606,607, mailed on May 14, 2019.
Office Action received for U.S. Appl. No. 15/611,344, mailed on Mar. 26, 2019.
Office Action received for U.S. Appl. No. 15/611,344, mailed on May 21, 2020.
Office Action received for U.S. Appl. No. 15/848,878, mailed on Feb. 5, 2020.
Office Action received for U.S. Appl. No. 15/848,878, mailed on Oct. 29, 2019.
Office Action received for U.S. Appl. No. 16/212,425, mailed on Mar. 16, 2020.
Office Action received for U.S. Appl. No. 12/753,855 mailed on May 5, 2016.
Office Action received for U.S. Appl. No. 13/901,375, mailed on Aug. 1, 2016.
Office Action received for U.S. Appl. No. 14/199,675, mailed on Nov. 3, 2016.
Office Action received for U.S. Appl. No. 15/611,328, mailed on Mar. 27, 2019.
Penumbra Augments Vascular Franchise with Latest Indigo System Launch and Expands Medical/Scientific Leadership, Jul. 14, 2020, https://www.penumbrainc.com/penumbra-augments-vascular-franchise-with-latest-indigo-system-launch-and-expands-medical-scientific-leadership/.
Strength of Materials/Torsion, Wikibooks, 3 pp., accessed Feb. 22, 2023 (en.wikibooks.org/wiki/Strength_of_Materials/Torsion) (last edited Feb. 1, 2022) (Year: 2022).
U.S. Appl. No. 12/753,836, Feb. 1, 2012, Office Action.
Final Office Action received for U.S. Appl. No. 17/154,777, mailed on Apr. 17, 2024, 17 pages.
Requirement for Restriction/Election received for U.S. Appl. No. 17/752,600, mailed on Apr. 25, 2024, 5 pages.
European Search Report received for EP Patent Application No. 23188821.5, mailed on Dec. 6, 2023, 7 pages.
Office Action received for European Patent Application No. 19710207.2, mailed on Dec. 4, 2023, 4 pages.
Supplementary European Search Report received for EP Patent Application No. 21744674.9, mailed on Feb. 7, 2024, 9 pages.
Non-Final Office Action received for U.S. Appl. No. 17/036,302, mailed on Nov. 6, 2025, 23 pages.
Non-Final Office Action received for U.S. Appl. No. 17/901,821, mailed on Jul. 15, 2025, 12 pages.
Final Office Action received for U.S. Appl. No. 17/901,821, mailed on Jan. 2, 2026, 6 pages.
Penumbra, Inc., Penumbra Augments Vascular Franchise with Latest Indigo System Launch and Expands Medical/Scientific Leadership, Jul. 14, 2020, https://www.penumbrainc.com/penumbra-augments-vascular-franchise-with-latest-indigo-system-launch-and-expands-medical-scientific-leadership/, May 14, 2026.

* cited by examiner

INTRAVASCULAR GUIDEWIRE AND MICROCATHETER SYSTEM

CROSS-REFERENCE TO RELATED APPLICATIONS

This application claims priority to and the benefit of U.S. Provisional Application No. 63/271,114, filed Oct. 22, 2021 and titled "Intravascular Guidewire and Microcatheter System," and to U.S. Provisional Application No. 63/240,845, filed on Sep. 3, 2021 and titled "Microcatheter Device with Non-Linear Bending Stiffness," each of which is incorporated herein by this reference in its entirety.

BACKGROUND

Interventional devices such as guidewires and catheters are frequently utilized in the medical field to perform delicate procedures deep within the human body. Typically, a catheter is inserted into a patient's femoral, radial, carotid, or jugular vessel and navigated through the patient's vasculature to the heart, brain, or other targeted anatomy over a guidewire. Once in place, the catheter can be used to deliver drugs, stents, embolic devices, radiopaque dyes, or other devices or substances for treating the patient in a desired manner.

In many applications, such an interventional device must be navigated through the tortuous bends and curves of a vasculature passageway to arrive at the targeted anatomy. Such an interventional device requires sufficient flexibility, particularly closer to its distal end, to navigate such tortuous pathways. However, other design aspects must also be considered. For example, the interventional device must also be able to provide sufficient torquability (i.e., the ability to transmit torque applied at the proximal end all the way to the distal end), pushability (i.e., the ability to transmit axial push to the distal end rather than bending and binding intermediate portions), and structural integrity for performing intended medical functions.

It is desirable for catheter devices to have good axial response, such that when a push force is applied to a proximal end of a catheter device positioned over a guidewire (e.g., within a patient's vasculature), the intermediate and distal portions of the catheter device advance over the guidewire in accordance with the push force (e.g., further into the patient's vasculature). Often, however, as the catheter device is advanced within the bends and curves of the vasculature, much of the axial movement incidentally pushes intermediate portions of the device into the walls of the curved portions of the vasculature rather than actually advancing the distal end of the catheter device forward. This lack of correspondence between the amount of axial push provided by the user at the proximal end and the resulting forward movement of the distal end makes navigation more difficult and less tactilely intuitive.

Accordingly, there exist several limitations in the field of guidewire and catheter systems, and there is an ongoing need, for example, for systems that enable effective routing of a catheter over a guidewire within the vasculature without requiring excessive push force to reach an intended anatomical target.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Overview of Combination Systems

Figure 1:
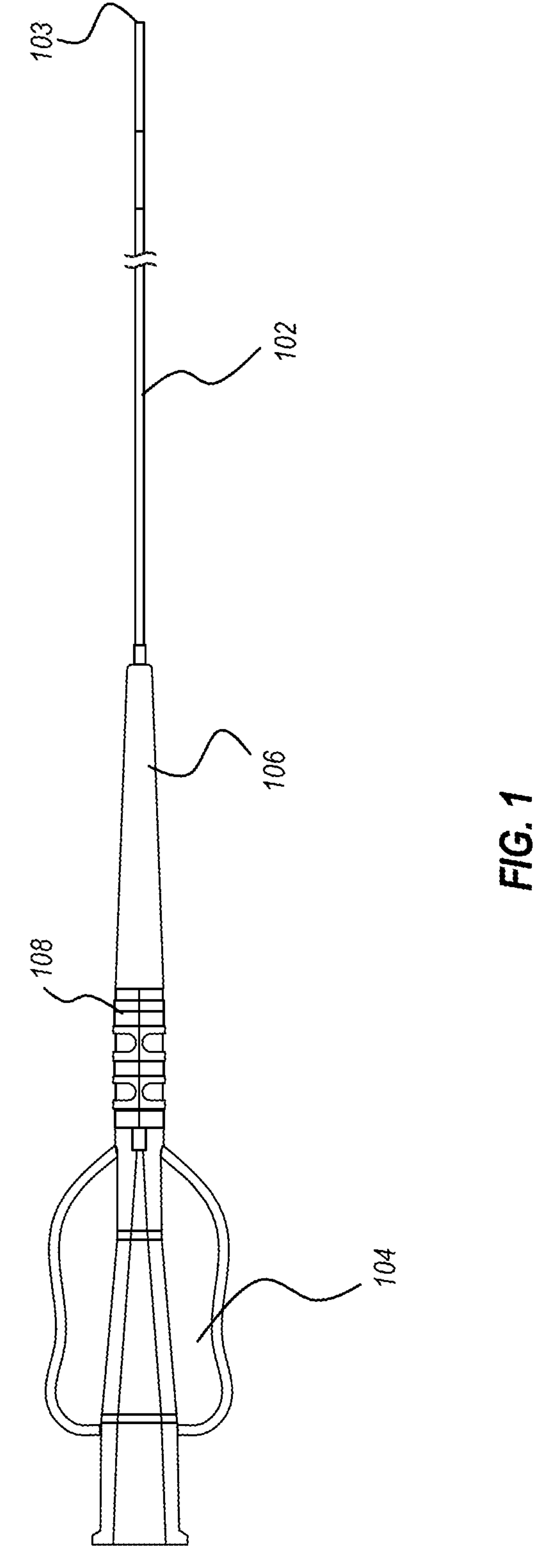
FIG. 1 illustrates an overview of a catheter system, including a catheter and hub.

As noted above, many catheter devices experience a lack of correspondence between application of proximal push force and advancement of distal and intermediate portions (e.g., when the catheter device is positioned over a guidewire within curved portions of a patient's vasculature). Conventional catheter devices often utilize multiple different materials to provide a gradient in bending stiffness from proximal end to distal end. However, whenever there is a transition between materials of differing stiffness, the bending, axial, and torsional stiffness profiles of the device include an abrupt step change. Such abrupt changes in bending stiffness are undesirable because they can concentrate mechanical stresses at particular locations, cause kink points, disrupt the smooth movement and bending of the device, and complicate navigation in tortuous vasculature. Such abrupt changes in bending stiffness can contribute to the lack of correspondence between proximal push force and distal advancement discussed above.

When faced with a situation in which applying excessive proximal push force (e.g., greater than about 30 to 50 grams) fails to sufficiently facilitate further advancement of a catheter device over a guidewire within a patient's vasculature, medical practitioners typically withdraw the catheter (and sometimes also the guidewire) to reattempt routing of the guidewire and/or the catheter through the patient's vasculature to reach the target. Such occurrences result in inefficiencies related to time and materials and may adversely affect patient outcomes.

Accordingly, at least one aspect of the present disclosure is to provide guidewire and catheter systems that can be used to facilitate desirable catheter axial response (e.g., pushability) for advancement through patient vasculature (or through environments that simulate patient vasculature). At least some of the example guidewire and catheter systems discussed herein exhibit a smooth bending stiffness profile along the length of the devices, thereby contributing to a reduction in concentration of mechanical stresses at particular locations. Such features may enable the catheter devices of the present disclosure to exhibit pushability, torquability, and/or bending flexibility characteristics that allow the catheter devices to advance over guidewires in a manner that reduces the loss of axial forces to the vasculature walls and contributes to effective routing (with minimal push force) to the intended target.

A catheter device constructed in accordance with the present disclosure may advance over a guidewire within the tortuous paths of a patient's vasculature in response to push forces of 50 g or below. For instance, for an example tortuous path model with a total path length of 21.5 cm, with inner diameter of 3.68 mm, with three full loops (each with a loop radius of 6.4 mm), guidewire and catheter systems constructed in accordance with the present disclosure were able to advance over a guidewire without exceeding 30 grams of push force, and in some instances without exceeding 20 grams of push force. In particular, a catheter/guidewire system with a 0.017 inch (inner diameter) catheter and 0.014 inch (outer diameter) guidewire was routed through the model with a push force not exceeding 18 g, and a catheter/guidewire system with a 0.027 inch (inner diameter) catheter and 0.024 inch (outer diameter) guidewire was routed through the model with a push force not exceeding 29 g.

Other device combinations, such as the STRYKER SYNCHRO 2 used in combination with the STRYKER EXCELSIOR SL-10 failed to achieve such performance. Indeed, the STRYKER SYNCHRO 2 and STRYKER EXCELSIOR SL-10 combination system was unable to proceed through the full model even though a push force of 50 g (which jumped to as high as 200 g) was applied.

The ratio of the model to the tested catheters was 557% (e.g., 3.68 mm inner diameter for the model and a 0.66 mm outer diameter for the catheter). Differently sized guidewire and catheter combinations utilizing the structural features disclosed herein are also expected to perform similarly in a model having similar size ratios. For example, similar effective results are expected so long as the ratio of the inner diameter of the model to the outer diameter of the catheter is about 250% to about 800%, or about 300% or 350% to about 750%, or about 400% to about 700%, or about 450% to about 650%, or about 500% to about 600%, or a ratio within a range with endpoints defined by any two of the foregoing values.

Thus, guidewire and catheter systems of the present disclosure enable medical practitioners to advance a catheter more effectively to an intended target, reducing situations where safe levels of push force fail to fully advance a catheter over a guidewire, thereby avoiding the inefficiencies associated with withdrawal and/or re-advancement of a catheter and/or guidewire device.

Tests similar to those demonstrated in FIGS. 5A through 5D have demonstrated that catheters constructed in accordance with the present disclosure (e.g., including one or more features described with reference to catheter 102) are able to advance over guidewires in vessels in response to application of a push force of about 50 g or below, or about 40 g or below, or about 35 g or below, or about 30 g or below, or about 25 g or below, or about 20 g or below (e.g., within a range of about 10 g to about 20 g, or a range of about 20 g to about 30 g, or a range of about 30 g to about 40 g, or a range of about 40 g to about 50 g, or a range with any of the foregoing values as endpoints).

Such functionality may be exhibited by catheter devices of the present disclosure in operating environments (e.g., real vessels or model vessels) of about 21.5 cm of path length (or more or less) with curves and/or loops (e.g., 1 curve and/or loop, 2 curves and/or loops, 3 curves and/or loops, or more than 3 curves and/or loops) of various radii (e.g., within a range of about 3 mm to about 10 mm, such as 6.4 mm).

The disclosed systems may be utilized in various vessel-to-catheter ratios. For instance, a vessel inner diameter may be within a range of about 2 mm to about 6 mm (e.g., about 3.68 mm), and a catheter outer diameter may be within a range of about 0.2 mm to about 1.5 mm (e.g., about 0.66 mm), resulting in a range of vessel-to-catheter ratios of about 133% to about 3,000% (e.g., about 371% or greater, such as 557% for a lumen inner diameter of 3.68 mm and a catheter outer diameter of 0.66 mm). Testing models may utilize other dimensions. One of skill in the art will recognize that various catheter/guidewire combinations can be effectively tested against each other using such testing models so long as the same model conditions are utilized for each catheter/guidewire combination. Such push force testing is readily within the capabilities of the skilled person.

Example Catheter Devices

FIG. 1 is an overview of an example catheter device 100 that includes features, described in more detail below, that provide one or more of improved axial responsiveness, improved distribution of bending forces, and/or a smooth device bending stiffness profile.

The catheter device 100 includes a catheter 102 connected to a hub 104 at a proximal end and extending therefrom to a distal end 103. The catheter 102 may be coupled to the hub 104 using adhesive, a friction fit, through insertion molding, and/or other appropriate attachment means. A strain-relief member 106 is also disposed over the proximal section of the catheter 102 near the hub 104. The strain-relief member 106 has an outer diameter that substantially matches the adjacent section of the hub 104. The strain-relief member 106 extends for a distance from the hub 104 with a substantially constant outer diameter before tapering distally to the end where the catheter 102 emerges and extends farther distally. The strain-relief member 106 may include a groove pattern 108, disposed at the section of substantially constant outer diameter, that functions to provide additional flexibility to the strain-relief member 106 and/or to provide surface features for enhancing user grip and tactile engagement.

The working length of the catheter 102 (i.e., the distance between the distal end of the strain-relief (106) and the catheter (102) distal end (103) may vary according to particular application needs. As an example, the catheter 102 may have a working length of about 50 cm to about 200 cm, though shorter or longer lengths may be utilized where appropriate. The catheter size (typically referring to the inner diameter/lumen size) may also vary according to particular application needs. Examples include 0.010 inches, 0.013 inches, 0.017 inches, 0.021 inches, 0.027 inches, 0.030 inches, 0.035 inches, 0.038 inches, 0.045 inches, 0.065 inches, 0.085 inches, 0.100 inches, or a range including any two of the foregoing values as endpoints. The inside diameter of the catheter can taper from a smaller distal portion to a larger proximal portion. Smaller or larger sizes may be utilized in some applications as appropriate.

Furthermore, the outer diameter of the catheter 102 may vary according to particular application needs. Examples include 0.010 inches, 0.013 inches, 0.017 inches, 0.021 inches, 0.026 inches, 0.027 inches, 0.030 inches, 0.035 inches, 0.038 inches, 0.045 inches, 0.065 inches, 0.085 inches, 0.100 inches, 0.135 inches, 0.165 inches, 0.20 inches, or a range including any two of the foregoing values as endpoints.

Although the distal section of the catheter 102 is shown in this example as having a straight shape, other embodiments may include a shaped distal tip. For example, the distal section of the catheter 102 may have an angled shape, a curved shape (e.g., 45 degree angle, 90 degree angle, J shape, etc.), a compound curved shape, or other appropriate angled or bent shape as known in the art.

The catheter device 100 described herein may be utilized for a variety of interventional applications, most commonly in cardiovascular, peripheral vascular, and neurovascular interventional procedures. Examples include accessing distal anatomy, crossing vessel lesions or blood clots, ischemic treatments, delivering therapeutic agents (e.g., embolic coils or other embolic agents), injecting diagnostic agents (e.g., contrast media or saline), retrieval applications, aspiration applications, or other applications where microcatheter use is beneficial.

Internal features of the catheter 102 are described in greater detail below. The outer surface of the catheter 102 may be coated with an appropriate coating material, such as a hydrophilic coating, to make the surface more lubricious. The coating material may cover substantially all of the working length of the catheter 102, or a portion thereof. For example, the coating material may be applied to the distal-most 30% to 80% of the working length of the catheter 102.

Figure 2:
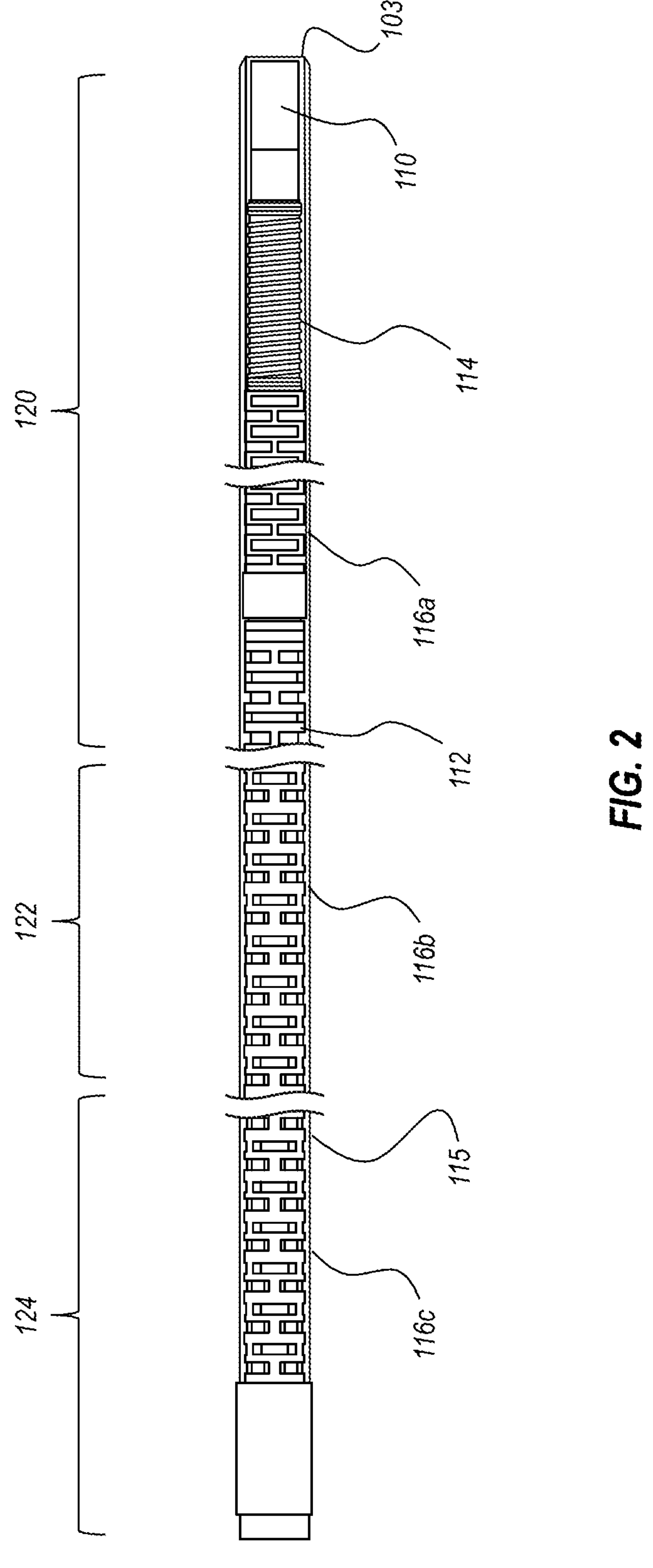
FIG. 2 illustrates a detailed view showing various sections of the catheter of the catheter system.

FIG. 2 illustrates a detailed view of the catheter 102, better showing some of the internal components and different longitudinal sections of the catheter 102. As shown, the catheter 102 includes an inner liner 110 that defines the inner lumen of the device. The liner 110 may be formed from polytetrafluoroethylene (PTFE) and/or other appropriate polymer. A coil 114 is positioned on the wire near the distal end 103. The coil 114 is attached to or positioned next to a microfabricated shaft 112 (also referred to herein as "inner shaft") that extends proximally therefrom. An outer member 115, formed from one or more polymer materials, is typically heat shrink laminated over and through the coil 114 and shaft 112, encasing both while also attaching to the liner.

In one embodiment, the coil 114 is formed from stainless steel and the shaft 112 is formed from nitinol. These materials, when used in combination with other features described herein, have been found to provide effective axial response, effective distribution of bending forces, and a smooth bending stiffness profile. Other embodiments may utilize one or more different materials for the coil 114, the shaft 112, or both. In some embodiments, for example, the shaft 112 may include other superelastic alloys and/or one or more polymers such as a polyether ether ketone (PEEK) or other polyaryl ether ketone (PAEK). In some embodiments, the coil 114 may include a superelastic alloy such as nitinol, one or more other metals, alloys, or polymers.

The catheter 102 is configured so that the overall bending stiffness profile transitions from higher stiffness (and less bending flexibility) at the proximal sections to lower stiffness (and greater bending flexibility) at the distal sections. In most applications, it is desirable to give the proximal sections of the device relatively high axial, torsional, and bending stiffness so they can provide good combination of flexibility, pushability, and torquability. Distal sections, however, are often navigated through tortuous vasculature and are thus preferably relatively more flexible in bending. This stiffness profile gradient can be created by adjusting certain features of the microfabricated shaft 112 and/or by utilizing different polymer materials to coat and embed the shaft 112 in the outer member 115. As explained in more detail below, in some embodiments, the microcatheter 112 and the outer member 115 are configured to work together to provide an overall stiffness profile that minimizes abrupt changes in stiffness and provides smooth stiffness transitions.

The illustrated embodiment includes a distal section 120, an intermediate section 122, and a proximal section 124. In the distal section 120, the outer member 115 is formed from a first polymer material **116*a*. In the intermediate section 122, the outer member 115 is formed from a second polymer material 116*b*. In the proximal section 124, the outer member 115 is formed from a third polymer material 116*c*. The polymer materials 116*a*, 116*b*, and 116*c* have different hardness and thus affect the stiffness of their respective sections differently. The second polymer material 116*b* has a higher hardness than the first polymer material 116*a*, and the third polymer material 116*c* has a higher hardness than the second polymer material 116*b***.

As one example of a set of polymer materials found to be effective when utilized together, the first polymer material **116*a* may have a Shore D hardness of about 20 to about 30, the second polymer material 116*b* may have a Shore D hardness of about 30 to about 50, and the third polymer material 116***c* may have a Shore D hardness of about 50 to about 80. Other embodiments may vary these values as desired such as softer in the distal portion, but the foregoing values have been found to be particularly effective. The polymer materials 116*a*, 116*b*, and 116*c* may be formed from independently from appropriate polymers such as polyether block amide (PEBA) polymers and can range in polymer durometers from Shore A hardness of about 10 to Shore D hardness of about 100.

The shaft 112 also includes features that provide variable bending stiffness. As shown, the shaft 112 is a tube structure that includes a series of microfabricated cuts. The cuts form axially extending "beams" that connect successive circumferentially extending "rings". These cut patterns can be varied to adjust the bending stiffness of the shaft 112. For example, the bending stiffness can be attuned by adjusting the number of beams that reside between each pair of adjacent rings. A "two-beam section", such as shown in the distal section 120, includes two beams between each pair of adjacent rings. A "three-beam section", such as shown in the intermediate section 122 and proximal section 124, includes three beams between each pair of adjacent rings. All else being equal (shaft material, cut depth, cut width, cut spacing), a three-beam section has greater bending stiffness than a two-beam section. A "one-beam section" with a single beam connecting adjacent rings may also be utilized, and will have even less bending stiffness than a two-beam section, all else being equal. A "four-beam section" and/or section having greater than four beams may also be utilized, and will accordingly provide greater bending stiffness as the number of beams between each pair of adjacent rings is increased.

Figure 3A:
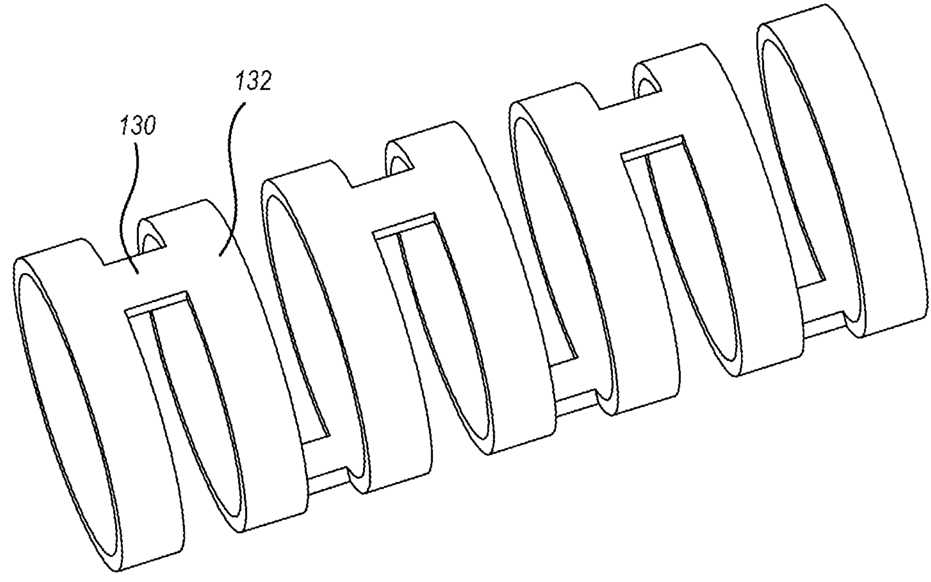
FIGS. 3A through 3C illustrate examples of a one-beam section, two-beam section, and three-beam section, respectively, that may be included in a microfabricated shaft used in the catheter system described herein.
Figure 3B:
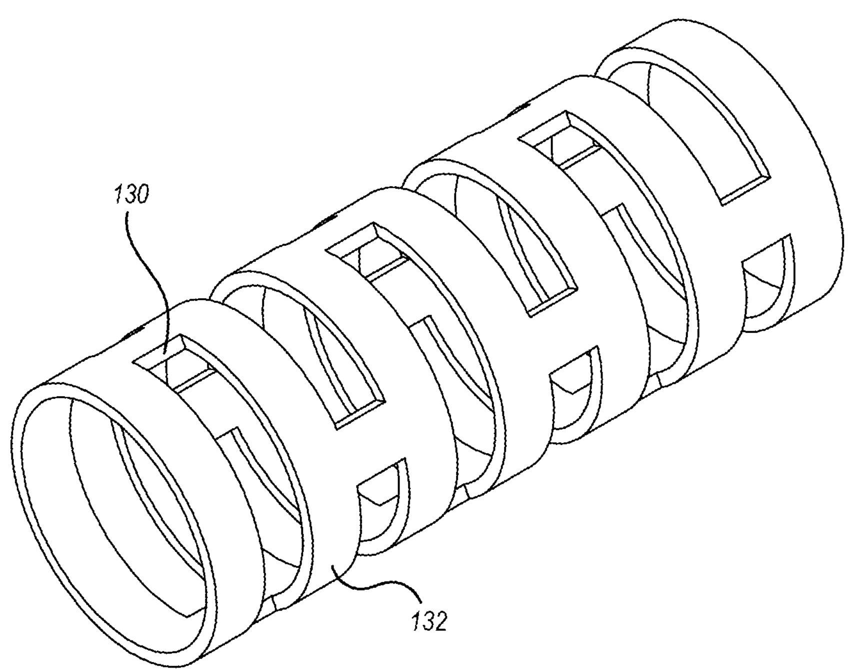
Figure 3C:
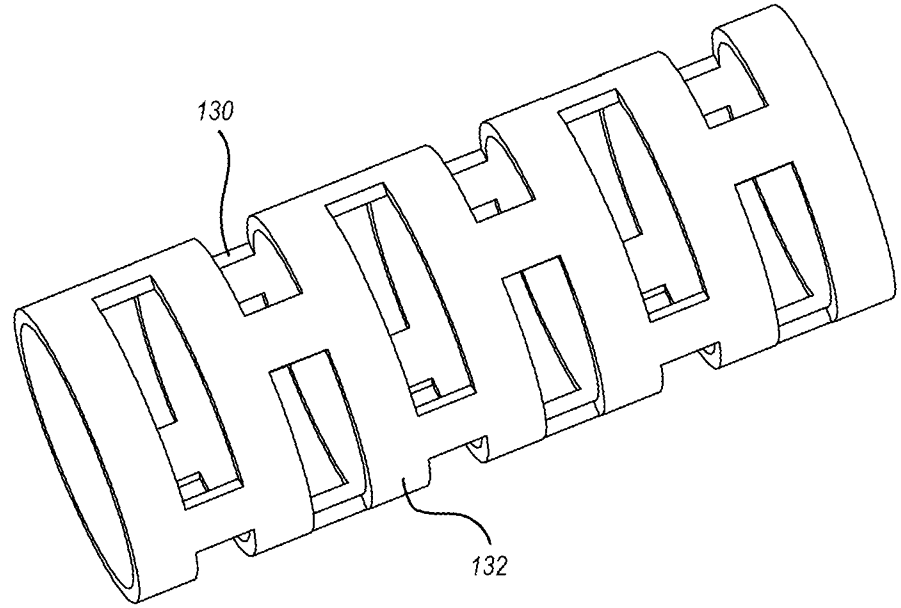

FIGS. 3A through 3C illustrate examples of a one-beam section, two-beam section, and three-beam section, respectively, showing example arrangements of beams 130 and rings 132 in such sections. The beams can be configured in a variety of arrangements depending on the angular offset (or lack thereof) between successive sets of beams and/or how frequently the angular offset is applied (e.g., after each ring or after two or more rings). The one-beam section of FIG. 3A, for example, includes a 180 degree angular offset from one beam to the next, the two-beam section of FIG. 3B includes a 90 degree offset from one beam pair to the next, and the three-beam section of FIG. 3C includes a 120 degree angular offset from one set of beams to the next. While these types of offsets are beneficial, they are also associated with preferred bending planes, and other arrangements may be provided to minimize or eliminate preferred bending planes. Examples include a helical arrangement, a distributed arrangement, an imperfect ramp arrangement, and a sawtooth arrangement. Additional details regarding beam arrangements that may be utilized in the presently disclosed shaft 102 are provided in U.S. Pat. No. 11,369,351 and in United States Patent Application No. 2022/0105312, each of which is incorporated herein by reference in its entirety.

In addition to adjusting the number of beams disposed between rings, the bending flexibility of the shaft 112 may be controlled by adjusting the depth of cuts, the width of cuts, and/or the spacing of cuts. Typically, the width of cuts is set at a given value (e.g., corresponding to a cutting blade size), and it is easier to adjust cut depth and/or cut spacing during manufacture in order to provide the desired control over the bending stiffness profile. All else being equal, as ring width is reduced (i.e., cut spacing is reduced), cut width is increased, and/or beam width is reduced (i.e., cut depth is increased), the resulting bending stiffness is reduced. In the illustrated embodiment, the spacing between cuts in the three-beam section (which is coincident with the intermediate section 122 and proximal section 124) is progressively reduced as it gets closer to the distal section 120. Similarly, the two-beam section (which is coincident with the distal section 120) begins with larger spaces between cuts and progresses to less space between cuts as it gets closer to the coil 114 and the distal end 103. Preferably, transitions between different geometries (e.g., three-beam to two-beam) are configured so that bending stiffness is the same or similar across the transition of these sections. The shaft 112 thus provides a stiffness gradient by way of transitioning from a three-beam section to a two-beam section, and also within the respective sections by way of transitioning from cuts that are more spaced apart to cuts that are relatively less spaced apart.

At the distal end of the two-beam section, the cut pattern is configured with relatively high flexibility in order to provide a smooth transition to the high flexibility of the coil 114. In some embodiments, the coil 114 is omitted and replaced by more of the two-beam section (or alternatively, a one-beam section) that extends to a position at or near the distal end 103.

The lengths of the sections 120, 122, and 124 may be varied according to particular application needs or preferences. In one embodiment, the distal section 120 may have a length of about 5 cm to about 40 cm, and the intermediate section 122 may have a length of about 10 cm to about 50 cm, with the proximal section 124 taking up the remainder of the working length of the catheter 102. The illustrated embodiment shows that the shaft 112 transitions from a three-beam configuration to a two-beam configuration at the transition of the intermediate section 122 to the distal section 120. However, the transitions of the shaft 112 need not necessarily correspond to the transitions of polymer material that define the separate sections 120, 122, and 124. As explained in more detail below, the shaft 112 and outer member 115 are configured together to compensate for and minimize abrupt stiffness changes, and in some instances, this may involve shaft transition zones that do not overlap completely with polymer transitions of the outer member 115.

Figure 4:
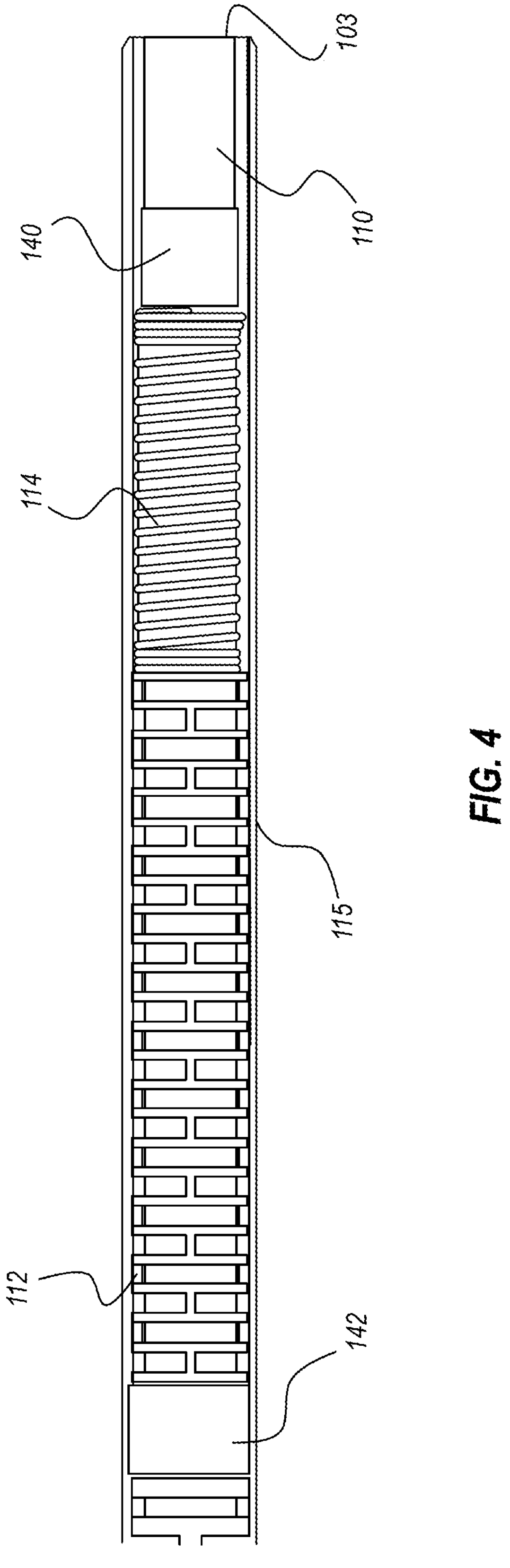
FIG. 4 illustrates a detailed view of a distal section of the catheter.

FIG. 4 illustrates a detailed view of the distal section 120 of the catheter 102, better showing certain distal features such as the liner 110, distal radiopaque marker band 140, coil 114, shaft 112, and proximal radiopaque marker band 142. The marker bands 140 and 142 are formed from a material more radiopaque than stainless steel. Examples include platinum, iridium, tungsten, other highly radiopaque metals, and alloys thereof. The distal marker band 140 provides an indication of the location of the distal end 103 of the catheter 102, whereas the proximal marker band 142 is offset by a predetermined length (e.g., 2 to 5 centimeters, or about 3 centimeters) to assist in proper positioning of detachable embolic coils or other components deployed through the catheter 102.

The shaft 112 may include a circumferential groove at the position where the proximal marker band 142 is placed. This groove can receive the marker band 142 such that the outer surface of the marker band 142 does not extend excessively beyond the outer diameter of the shaft 112. Once covered by the outer member 115, the outer diameter of the device over the proximal marker band 142 remains substantially flush.

In the illustrated embodiment, the coil 114 is variably pitched. Each end of the coil 114 includes a region of narrowed pitch that provides more improved transitions in bending stiffness from one geometry to another such as where the coil transitions to a microfabricated tube. As an example, the coil 114 may have a length of about 1 cm to about 3 cm. As shown, a portion of the liner 110 may extend a distance distally from the coil 114 and distal marker coil 140. This distance may vary from about 0.2 mm to about 2 mm, for example.

Catheter Bending Force Distribution

Figure 5A:
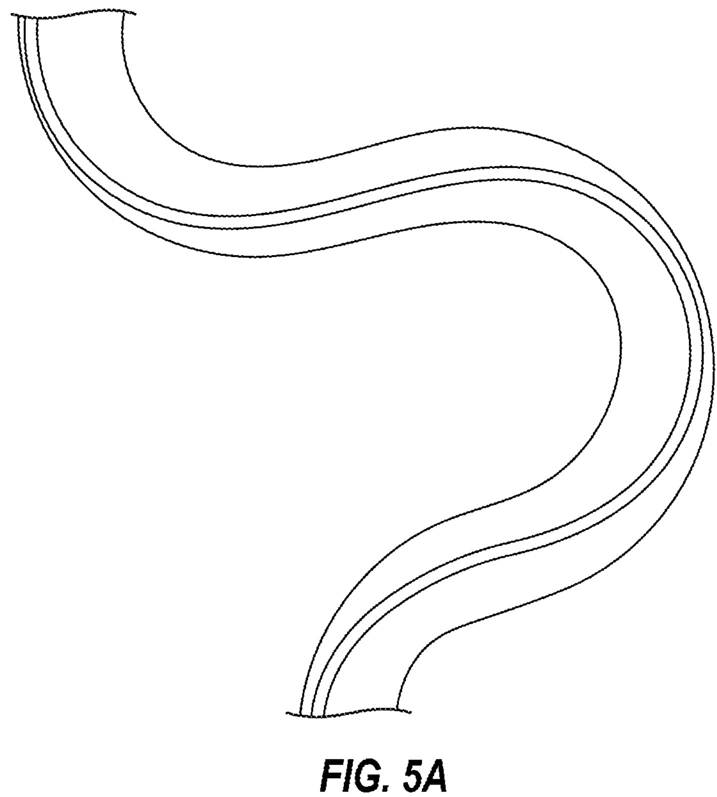
FIGS. 5A through 5D are photographs illustrating differences in axial response that can occur within a vessel (artificial vessel shown), with FIGS. 5A and 5B showing the axial response of a conventional catheter and FIGS. 5C and 5D showing the improved axial response of a catheter according to the present disclosure.
Figure 5B:
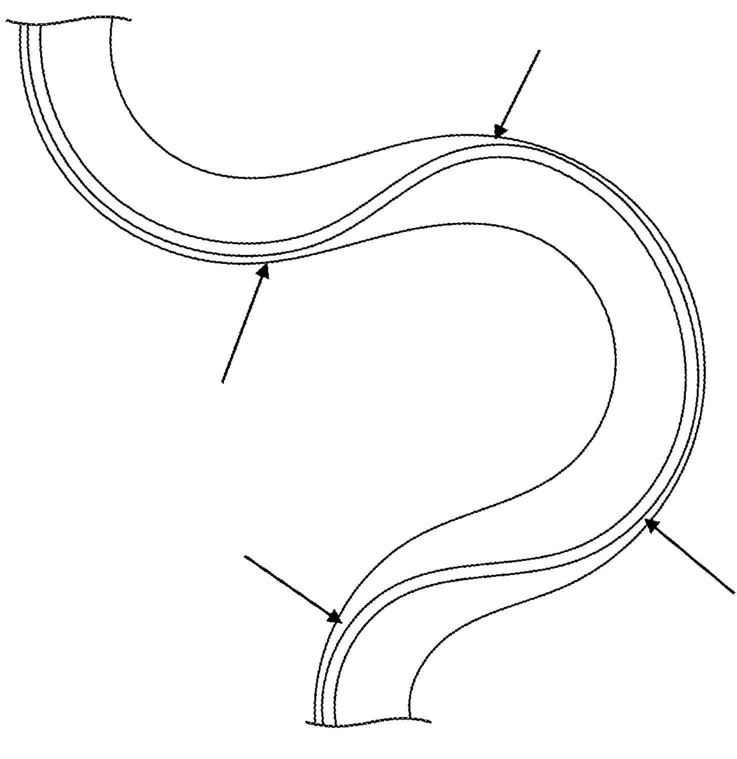

The catheter devices described herein include features that effectively distribute bending forces and thereby provide improved axial response in use. FIGS. 5A and 5B illustrate a common limitation in navigating a conventional catheter (a STRYKER EXCELSIOR SL-10 shown in this example) through an artificial vasculature construct. As the catheter approaches a bend in a vessel, a certain length of the catheter extends around the bend (initial position in FIG. 5A). Upon further pushing, the initial axial movement is taken up in pushing the catheter against the walls of the vessel to fill the curves (after push position in FIG. 5B; see contact points indicated by arrows) before any continued pushing results in actually advancing the distal tip of the catheter through the vasculature. This reduced correspondence between the amount of axial push provided by the user at the proximal end and the resulting forward movement of the distal end makes navigation more difficult and less tactilely intuitive. Furthermore, as noted above, practitioners are, in many instances, unable to apply additional push force to overcome the resistance presented by the vessel walls, as doing so would run the risk of patient injury.

In contrast to the response of conventional catheters as in FIGS. 5A and 5B, FIGS. 5C and 5D show navigation of the bend of the vessel using the catheter 102 as described herein. As shown, from the "initial" position (FIG. 5C) to the after-push position (FIG. 5D), less of the axial movement is taken up in filling the curve of the vessel, and more of the axial movement is thus transferred to actual movement of the distal end of the catheter 102. This function stems from the improved ability to distribute bending forces along the length of the catheter 102. By better distributing the bending forces, the catheter 102 better resists bending at any one particular location and can thereby better transfer proximal axial movement to the distal end of the device.

Figure 6:
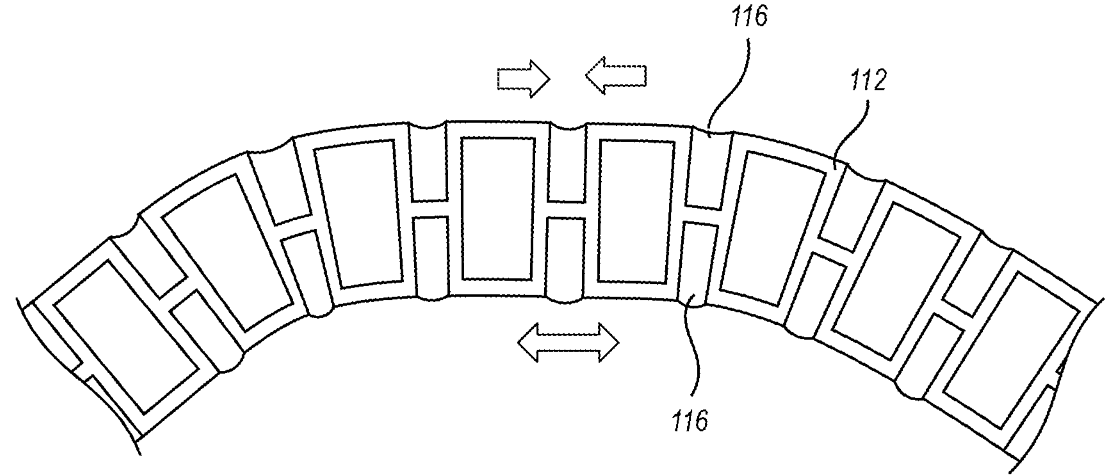
FIG. 6 schematically illustrates a section of the catheter during bending, showing how the catheter is configured to distribute bending, torsional, and axial forces in tortuous anatomy.

FIG. 6 further illustrates the ability of the catheter 102 to effectively distribute bending forces. FIG. 6 illustrates a portion of the shaft 112 during bending. The polymer material 116 fills the gaps between beams and rings of the shaft 112. For ease of viewing, the polymer material 116 is shown in discrete sections within each of the gaps of the shaft 112. In most cases, the polymer material 116 will fill the gaps, fuse with the liner 110, and also extend over the outer surface of the shaft 112 to fully encapsulate and embed the shaft 112.

During bending of the shaft 112, the shaft structure locally resists more bending stresses and distributes this stress to adjacent portions of the structure more effectively as compared to a coil or braid which are less likely to distribute bending stresses and more likely to kink. Additionally, the polymer material 116 effectively functions as a series of dampers each positioned between adjacent rings of the shaft 112. On the inner side of the bend, the polymer material 116 is compressed, and therefore provides a counteracting force that pushes outward against the rings and resists further bending. Similarly, on the outer side of the bend, the polymer material 116 is placed in tension, and therefore provides a counteracting force that pulls the rings inward and resists further bending. The bending stiffness of the catheter 102 is non-linear because it becomes increasingly resistant to bending, in a non-linear manner, as the bend angle is increased.

Figure 5C:
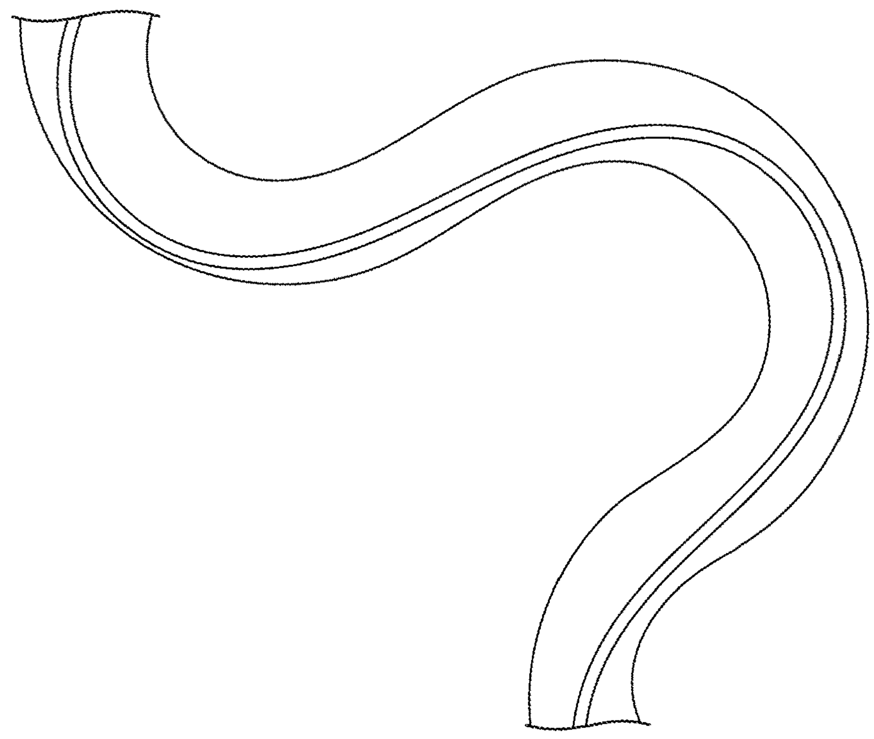
Figure 5D:
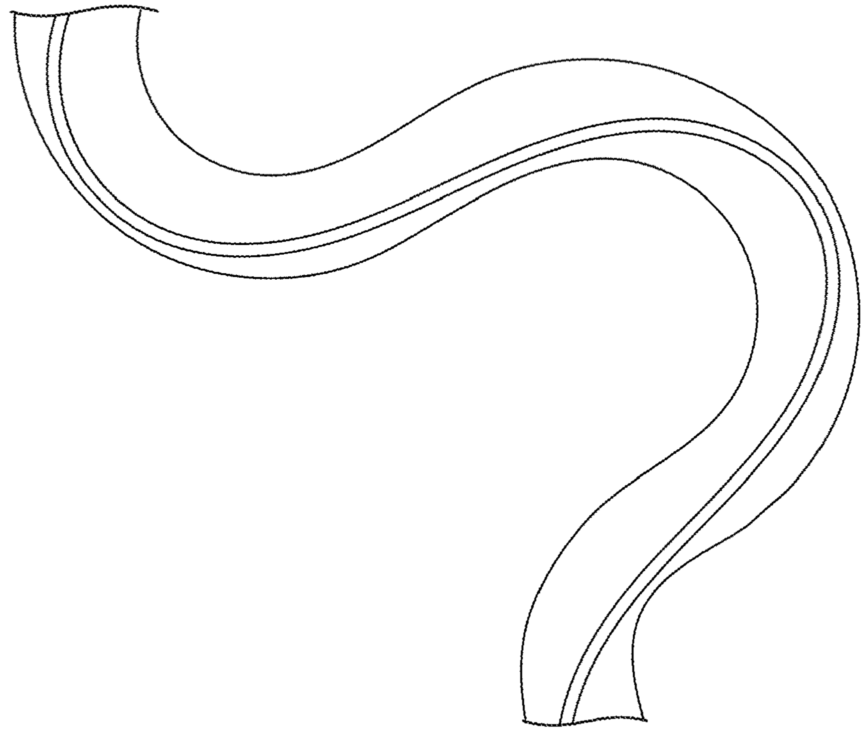

During bending, a conventional catheter will begin to bend at the apex and the cross-sectional shape of the catheter may tend to "ovalize". Once ovalization begins, resistance to bending decreases and it therefore becomes increasingly easier to bend with continued application of bending forces. In contrast, in the disclosed catheter 102, the bending resistance provided by the action of the microfabricated structure and polymer material 116 against the shaft 112 tends to distribute bending forces along the axial length of the catheter 102 and avoid ovalization and concentration of bending forces at a particular kink point. For example, the bending resistance will tend to spread a bend out to a larger radius of curvature rather than concentrating the bend at specific point thereby creating a kink location. The bending resistance provided by the catheter structure can therefore provide enhanced axial responsiveness (as illustrated by FIGS. 5C and 5D) and also enhanced protection against mechanical fatigue caused by bending stresses.

Smoothing of Catheter Bending Stiffness Profiles

Figure 7A:
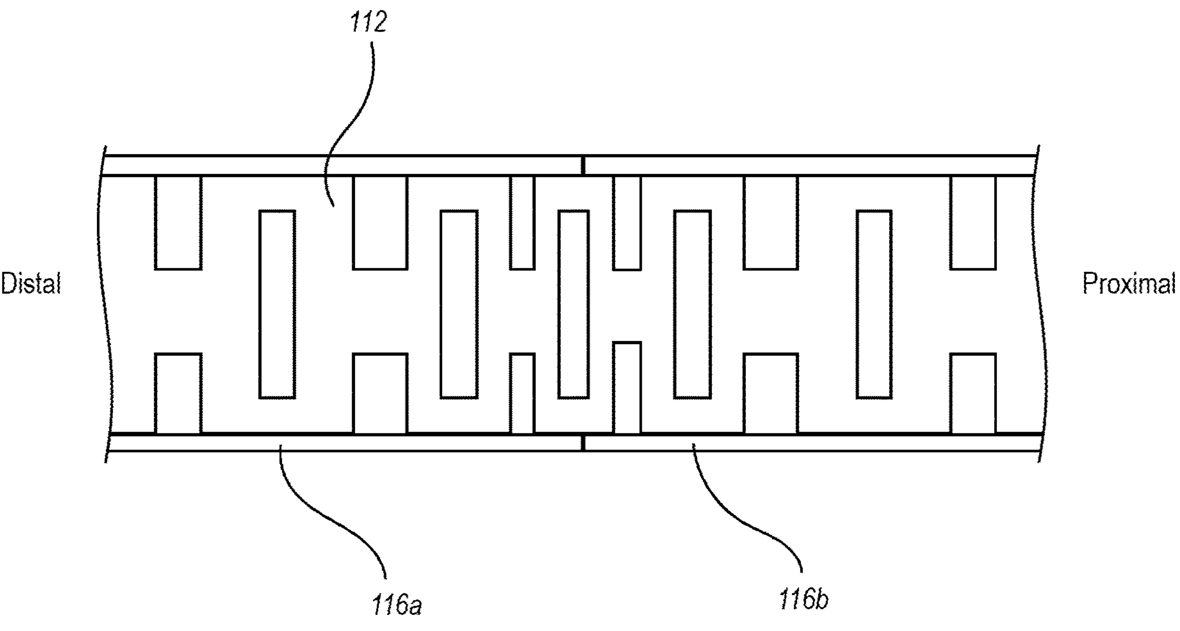
FIGS. 7A and 7B illustrate that the microfabricated shaft is configured to compensate for step changes in stiffness in the outer polymer layer due to transition from one polymer to another.
Figure 7B:
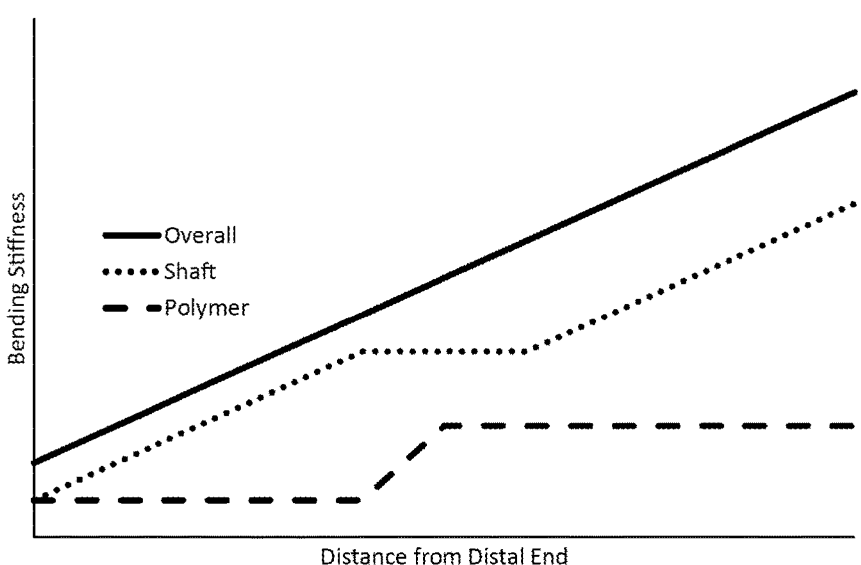

FIGS. 7A and 7B illustrate that the microfabricated shaft may be configured to compensate for step changes in stiffness in the outer member due to transition from one polymer to another. FIG. 7A illustrates a portion of the catheter 102 where the first polymer material 116*a* meets the second polymer material 116*b*. As shown in FIG. 7B, this is associated with an abrupt step change in the bending stiffness of the polymer layer of the outer member. Such abrupt changes in bending stiffness are undesirable because they can concentrate mechanical stresses, cause kink points, disrupt the smooth movement and bending of the device, and complicate navigation in tortuous vasculature.

To compensate for this step change, the shaft is configured such that the bending stiffness changes complement and compensate for the abrupt change in bending stiffness of the polymer outer member. As a result, the overall bending stiffness of the catheter remains relatively smooth across the transition from the first polymer 116*a* to the second polymer 116*b*. Similar configurations can be utilized at other polymer transition zones to minimize and smooth out abrupt step changes in bending stiffness. The shaft 112 can be configured to compensate for the step change in a variety of ways. In the example of FIG. 7A, because the bending stiffness of the second polymer 116*b* is higher than the first polymer 116*a*, the configuration of the cuts/gaps of the shaft 112 remain constant or are narrowed for a short distance across the transition before spreading out again to generally increase shaft bending stiffness while moving further proximally. Other means of adjusting the bending stiffness of the shaft 112 as described herein (e.g., adjusting the number of beams and/or cut depth) may additionally or alternatively be used to achieve the result of smoothing the overall bending stiffness profile.

Configuring the shaft 112 to compensate for abrupt bending stiffness changes of the polymer outer member 115 beneficially avoids the complications of other conventional approaches to smoothing out such transitions. Prior approaches rely on complicated splicing arrangements or polymer co-extrusion and mixing techniques. These add layers of extra complication to the manufacturing process and may still only marginally resolve the abruptness of the transition. Other approaches utilize different diameters of polymer tubing and diameter gradients to compensate for transitions between polymer types. However, these approaches result in an uneven outer diameter or add the requirement to somehow manage this by overlaying even more material.

Figure 8A:
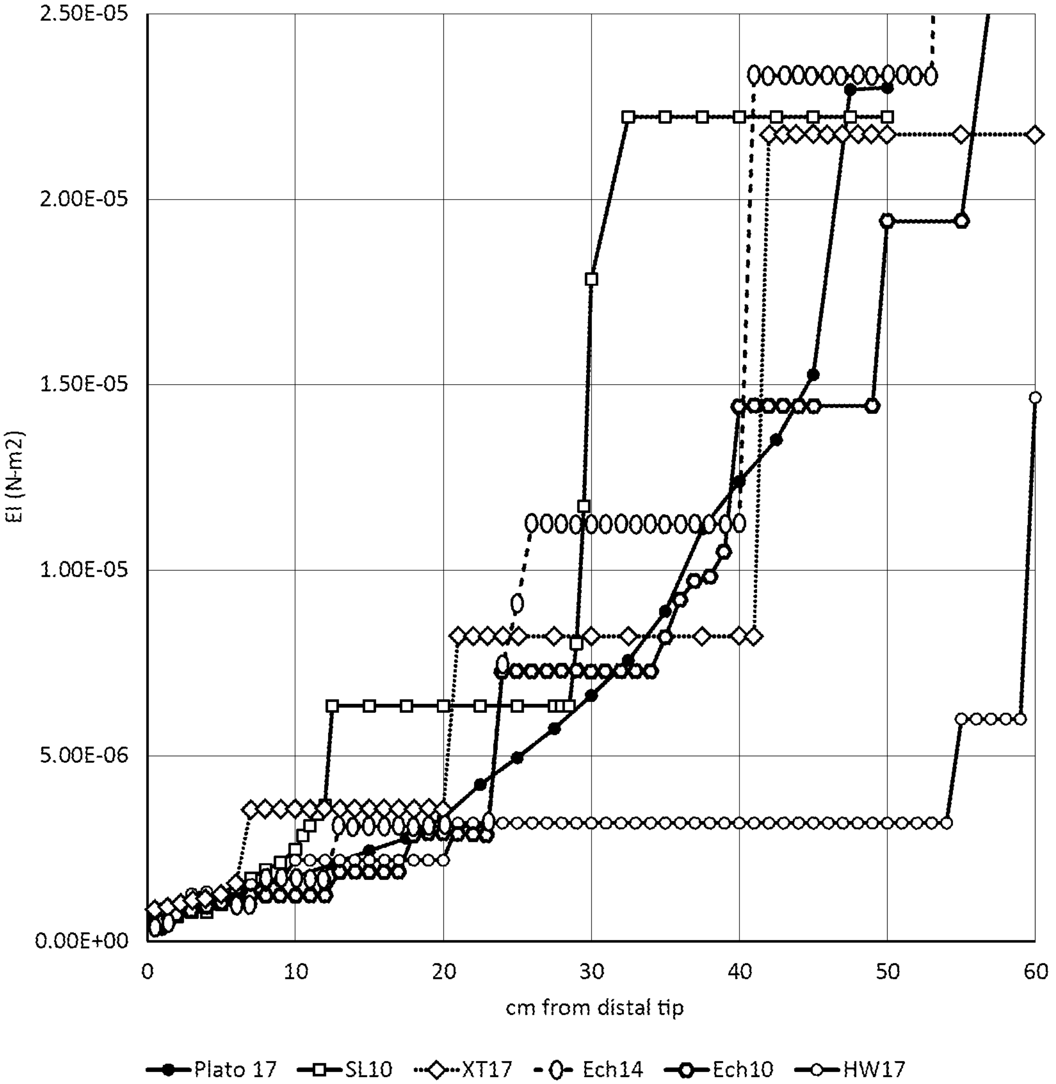
FIGS. 8A and 8B compare a bending stiffness profile of a catheter device according to the present disclosure (labelled "Plato 17") with bending stiffness profiles of various conventional catheter devices, with FIG. 8A showing bending stiffness up to 60 cm from the distal tip and FIG. 8B showing bending stiffness up to 15 cm from the distal tip.
Figure 8B:
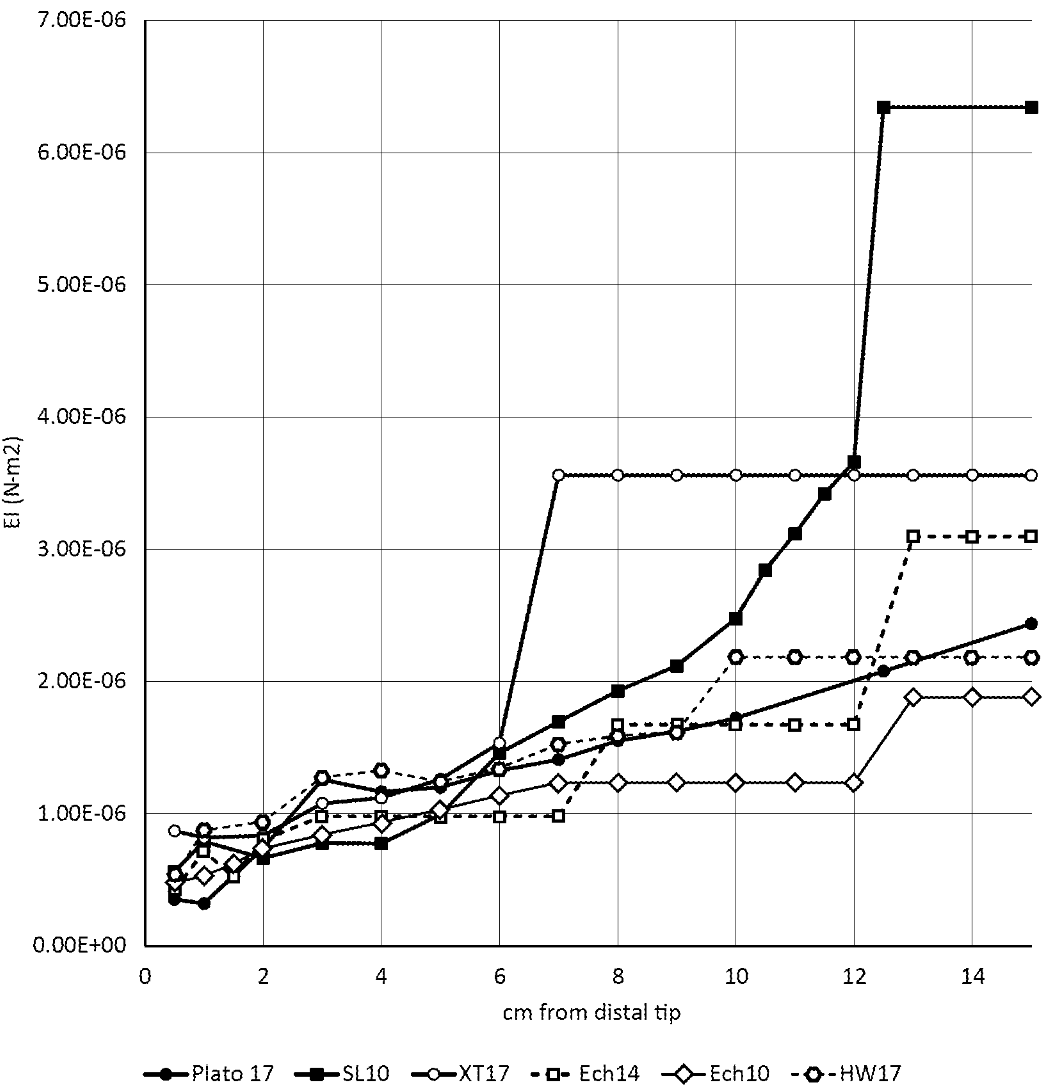

The smoothing features described herein enable the manufacture of microcatheters having improved bending stiffness profiles as compared to conventional microcatheters. FIGS. 8A and 8B illustrate the results of testing comparing the bending stiffness profile of a catheter made according to the present disclosure (labelled "Plato 17") to the bending stiffness profiles of several conventional microcatheters. In the Figures, "SL10" refers to an Excelsior SL-10 (sold by Stryker Neurovascular), "XT17" refers to an Excelsior XT-17 (sold by Stryker Neurovascular), "Ech14" refers to an Echelon 14 (sold by Medtronic), "Ech10" refers to an Echelon 10 (sold by Medtronic), and "HW17" refers to a Headway 17 (sold by MicroVention Terumo). FIG. 8A illustrates bending stiffness profiles over the distal 50 to 60 cm of the devices, FIG. 8B provides a closer view of the bending stiffness profiles over the distal 15 cm of the devices. In the Figures, the Plato 17 data represents an average of 5 replicates, the SL10 data represents an average of 3 replicates, the XT17 represents an average of 2 replicates, the Ech14 represents an average of 2 replicates, the Ech10 represents an average of 3 replicates, and the HW17 represents an average of 2 replicates. As shown, the catheter corresponding to the present disclosure provides a smoother profile with less abrupt changes in bending stiffness.

Table 1 presents the data of FIGS. 8A and 8B by listing different distal section sizes and providing the highest measured "slope" within that section. The "slope" represents the change in bending stiffness ($N \cdot m^2$) over the distance between measured data points (cm). As evident from the data points in FIGS. 8A and 8B, note that measurements were taken at increments of 0.5 cm to 2.5 cm, usually every 1 cm with smaller increments at regions where a clear polymer transition was evident and larger increments once reaching about 15 to 20 cm from the distal end. The slope therefore provides an indication of the abruptness of bending stiffness changes across the given section of the catheter.

TABLE 1

Stiffness Changes of Various Microcatheters Across Different Distal Section Sizes.

| Section Measured from Distal End (cm) | Highest Measured "Slope" Within Section ($(N \cdot m^2)/cm$) |
|---|---|
| Plato 17 | |
| 0-15 | $5.20e^{-7}$ |
| 0-35 | $5.20e^{-7}$ |
| 0-50 | $8.91e^{-7}$ |
| SL-10 | |
| 0-15 | $5.37e^{-6}$ |
| 0-35 | $1.22e^{-5}$ |
| 0-50 | $1.22e^{-5}$ |
| XT-17 | |
| 0-15 | $2.03e^{-6}$ |
| 0-35 | $4.65e^{-6}$ |
| 0-50 | $1.35e^{-5}$ |
| Echelon-14 | |
| 0-15 | $1.42e^{-6}$ |
| 0-35 | $4.32e^{-6}$ |
| 0-50 | $1.21e^{-5}$ |
| Echelon-10 | |
| 0-15 | $6.46e^{-7}$ |
| 0-35 | $4.39e^{-6}$ |
| 0-50 | $4.97e^{-6}$ |
| Headway-17 | |
| 0-15 | $7.05e^{-7}$ |
| 0-35 | $1.00e^{-6}$ |
| 0-50 | $1.00e^{-6}$ |

As shown, the Plato 17 has the lowest measured slope across the distal 15 cm section, across the distal 35 cm section, and across the distal 50 cm section. Based on the data of FIGS. 8A and 8B, as further disclosed in Table 1, in some embodiments a catheter device as described herein has a bending stiffness slope ($(N \cdot m^2)/cm$)) of no more than about $6.0 \times 10^{-7}$ for a distal 15 cm section, no more than about $9.0 \times 10^{-7}$ for a distal 35 cm section, and/or no more than about $9.0 \times 10^{-7}$ for a distal 50 cm section. While the Plato 17 device configured according to the present disclosure achieved each of the foregoing features, none of the other prior catheter devices tested were able to do so.

In some embodiments, at least a portion of the distal 35 cm of the catheter device has a bending stiffness of $5 \times 10^{-6}$ $N \cdot m^2$ or greater. In some embodiments, in addition to the foregoing stiffness minimum, a catheter device as described herein has a bending stiffness slope ($(N \cdot m^2)/cm$)) of no more than about $4.0 \times 10^{-6}$ for a distal 35 cm section and/or no more than about $4.5 \times 10^{-6}$ for a distal 50 cm section. As shown in FIGS. 8A and 8B and Table 1, while the Plato 17 device meets these requirements, the Headway-17 catheter does not meet the minimum bending stiffness requirement, and none of the other tested catheters meet the slope requirements.

Figure 9:
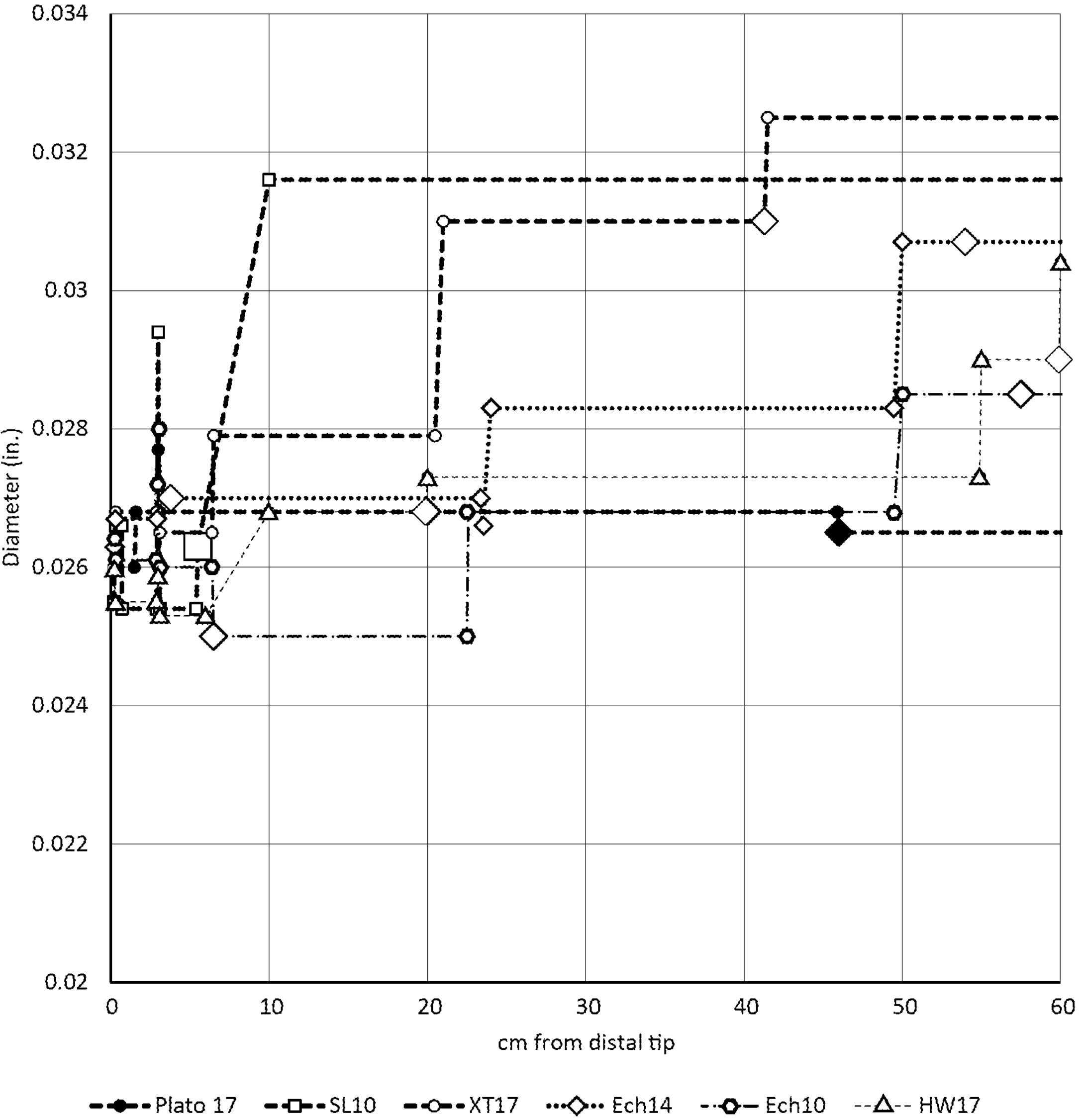
FIG. 9 compares outer diameters along distal lengths of a catheter device according to the present disclosure (labelled "Plato 17") to various conventional catheter devices.

FIG. 9 compares outer diameters along distal lengths of the Plato 17 device according to the present disclosure to various conventional catheter devices. The larger data points represent points where a polymer transition is visibly apparent. The data from FIG. 9 is also represented in Table 2, which shows the maximum diameter change within the distal 15 cm section and the distal 35 cm section of each of the catheter devices. As shown, the Plato 17 diameter changes by no more than 0.0017 inches across the distal 15 cm section and across the distal 35 cm section.

TABLE 2

Diameter Changes of Various Microcatheters Across Different Distal Section Sizes.

| Section Measured from Distal End (cm) | Maximum Diameter Change (inches) |
|---|---|
| Plato 17 | |
| 0-15 | .0017 |
| 0-35 | .0017 |
| SL-10 | |
| 0-15 | .0062 |
| 0-35 | .0062 |

TABLE 2-continued

Diameter Changes of Various Microcatheters Across Different Distal Section Sizes.

| Section Measured from Distal End (cm) | Maximum Diameter Change (inches) |
|---|---|
| XT-17 | |
| 0-15 | .0024 |
| 0-35 | .0055 |
| Echelon-14 | |
| 0-15 | .0017 |
| 0-35 | .0020 |
| Echelon-10 | |
| 0-15 | .0022 |
| 0-35 | .0022 |
| Headway-17 | |
| 0-15 | .0015 |
| 0-35 | .0020 |

In some embodiments, a catheter device as described herein has (1) a bending stiffness of $5\times10^{-6}$ N·m$^2$ or greater in at least a portion of the distal 35 cm of the catheter device, (2) a change in outer diameter of no more than 0.002 inches across the distal 15 cm and/or distal 35 cm section, and (3) a bending stiffness slope ((N·m$^2$)/cm)) of no more than about $1.3\times10^{-6}$ for a distal 15 cm section, no more than about $4.2\times10^{-6}$ for a distal 35 cm section, and/or no more than about $1.1\times10^{-5}$ for a distal 50 cm section. While the Plato 17 device configured according to the present disclosure achieved each of the foregoing features, none of the other prior catheter devices tested were able to do so. That is, the Headway-17 catheter does not meet the minimum bending stiffness requirement, the Echelon-10 does meet the diameter change requirement, and none of the other tested catheters meet the slope requirements.

In some embodiments, the beneficial bending stiffness profile features described above are specifically applicable to a transition section where a first polymer of the outer member transitions to a second polymer of the outer member.

In some embodiments, the shaft 112 maintains substantially the same wall thickness along its length. Other catheter devices based on coils and/or braids will most often have adjusted wall thicknesses at transition points. Changes in wall thickness can introduce additional kink or stress points and/or require additional manufacturing steps to manage.

In some embodiments, there may be an acceptable bending stiffness change associated with the distal tip region because the shaft 112 transitions to the coil 114 and/or the coil 114 transitions to the distal-most section of liner 110. These stiffness changes may be acceptable because they are so near the distal end 103. Thus, in some embodiments, the distal-most 3 to 5 cm may be excepted from the foregoing bending stiffness change limits.

Catheter Fatigue Resistance

The catheter devices described herein also beneficially provide effective fatigue resistance. For example, in a bend and twist fatigue test method based on ASTM E2948, catheter devices as described herein are capable of achieving greater than 20 cycles before breaking. The bend and twist fatigue test method is described in more detail in document TM-00127, which is attached hereto as Appendix 1. In short, the test is adapted from ASTM E2948, which is a standard test method for measuring rotating bending fatigue of solid round fine wire.

The effective fatigue resistance of the disclosed catheter devices may be present along the entire length of the shaft portion of the device, or along one or more sub-sections of the device (e.g., along one or more sections having length of about 3 to 35 cm, or about 3 to 20 cm, or about 3 to 10 cm). The effective fatigue resistance is provided by one or more of the following parameters: (1) maintaining ring widths at less than or equal to about 30% of the corresponding outer diameter of the shaft 112; and/or (2) maintaining cut depths at greater than or equal to about 11% of the outer diameter of the shaft 112.

Example Guidewires

As noted hereinabove, the catheter devices of the present disclosure may operate in combination with various guidewire devices to achieve the benefits described herein (e.g., advancement of the catheter device over a guidewire device within a tortuous path by application of push force of 50 g or lower on the proximal portion of the catheter device).

FIGS. 10 through 20 illustrate components and aspects of example guidewires that may be utilized in combination with the catheter devices described hereinabove. Although FIGS. 10 through 20 focus, in at least some respects, on guidewire devices including manually shapeable tips and/or particular cut patterns, one will appreciate, in view of the present disclosure, that a guidewire device for use in combination with the catheter devices of the present disclosure may include additional or alternative features and/or components.

Examples of guidewire features and components that may be utilized by guidewires of the disclosed guidewire and catheter systems are described in in U.S. Pat. No. 11,369,351 (disclosing distributed, imperfect ramp, and sawtooth cutting patterns for guidewire tubes), United States Patent Application No. 2021/0228845 (describing guidewire devices in which the outer diameter of the tube is greater than the outer diameter of the proximal section of the core and including various coil configurations to provide centering of the distal section of the core within the tube), and United States Patent Application No. 2021/0346656 (describing guidewire devices with high ratios of torsional stiffness to lateral bending stiffness), each of which is incorporated herein by reference in its entirety.

Figure 10:
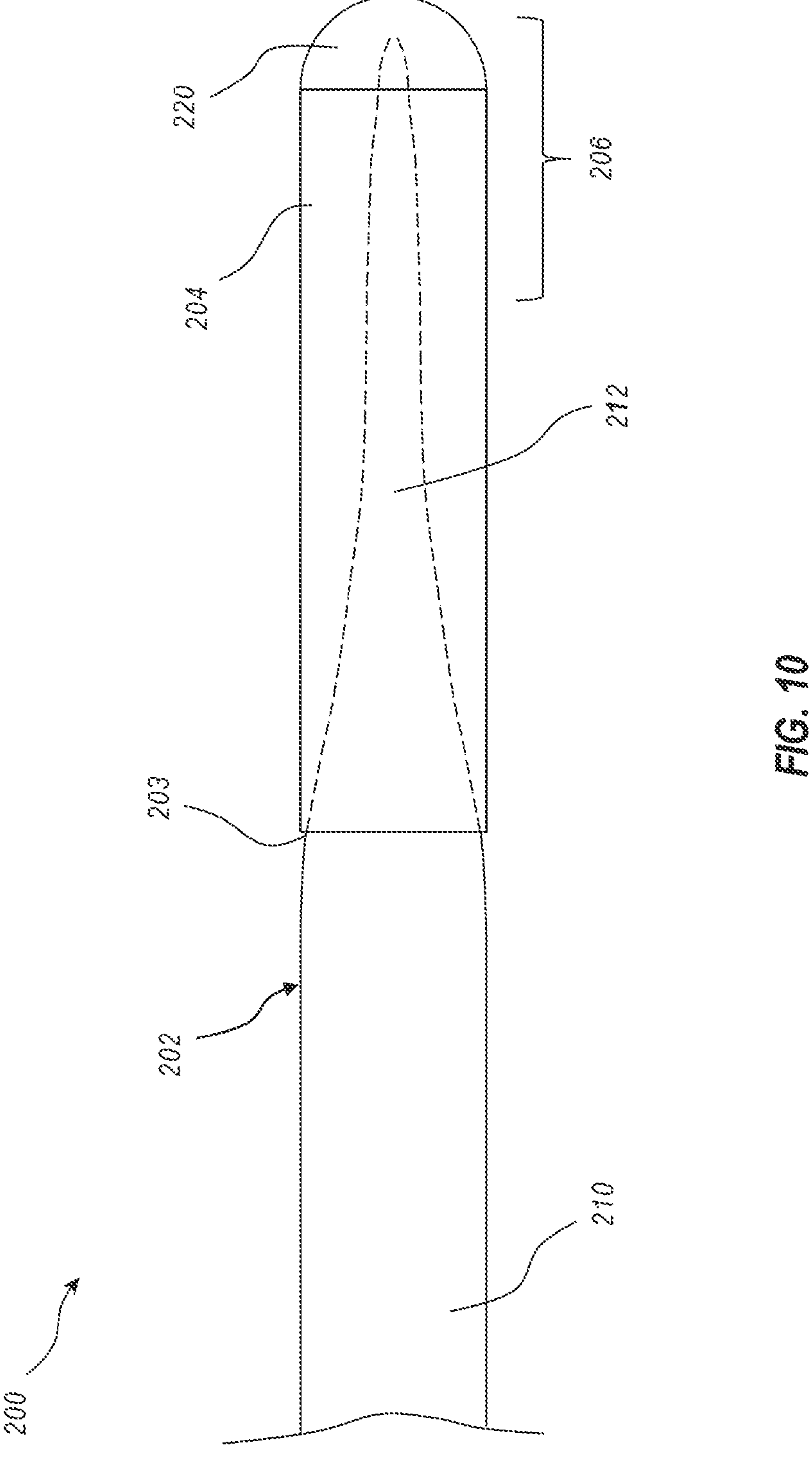
FIG. 10 illustrates an example embodiment of a guidewire device providing effective torquability and having a shapeable tip.

FIG. 10 illustrates an example guidewire device 200 having a core 202. A tube 204 is coupled to the core 202 and extends distally from a point of attachment 203 to the core 202. As shown, a distal section of the core 202 extends into the tube 204 and is surrounded by the tube 204. In some embodiments, the core 202 includes one or more tapering sections so that the core 202 is able to fit within and extend into the tube 204. For example, the distal section of the core 202 may be ground so as to progressively taper to a smaller diameter at the distal end. In this example, the core 202 and the tube 204 have substantially similar outer diameters at the attachment point 203 where they adjoin and attach to one another. In some embodiments, the core 202 and the tube 204 have different outer diameters at the attachment point 203 where they adjoin and attach to one another, with the difference in diameter being compensated for by a weld, solder, adhesive, interference fit, or other means of structural attachment.

Figure 12:
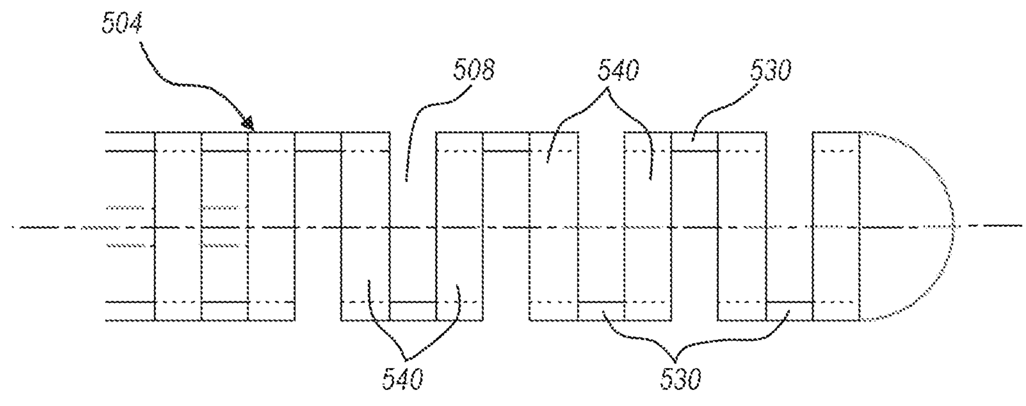
FIG. 12 illustrates an example embodiment of a tube structure which may be utilized with the guidewire device of FIGS. 10 and 11, the tube having a bypass cut pattern (i.e., one-beam cut pattern) configured to provide effective flexibility and shapeability of the distal tip.
Figure 13:
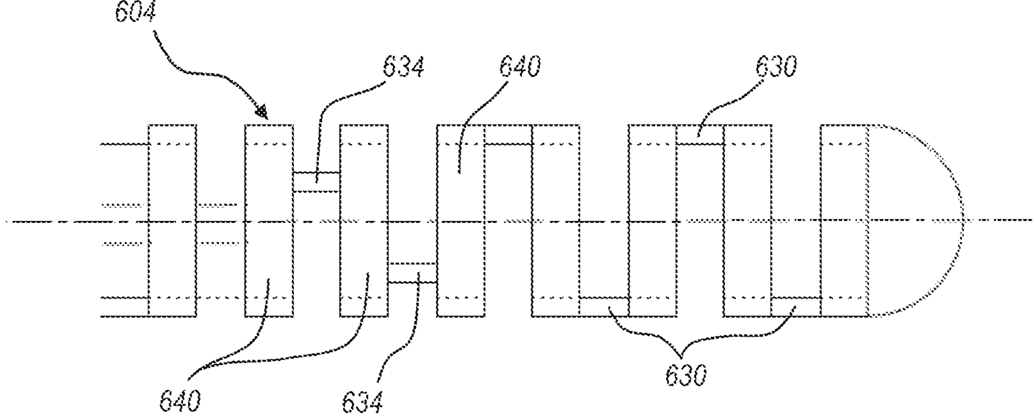
FIG. 13 illustrates an alternative embodiment of a tube structure including a section having an alternative one-beam cut pattern.
Figure 14:
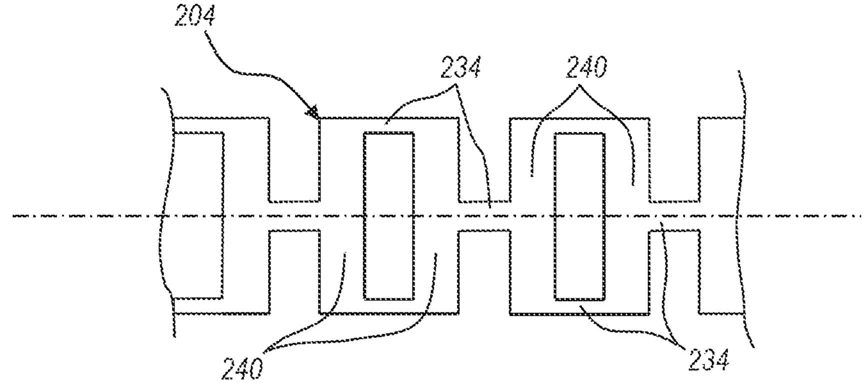
FIG. 14 illustrates an embodiment of a tube structure including a two-beam cut pattern with symmetrically spaced opposing beams.

The tube 204 is coupled to the core 202 (e.g., using adhesive, soldering, and/or welding) in a manner that allows torsional forces to be transmitted from the core 202 to the tube 204 and thereby to be further transmitted distally by the tube 204. A medical grade adhesive 220 may be used to couple the tube 204 to the core wire 202 at the distal end of the device and to form an atraumatic covering. As explained in more detail below, the tube 204 is micro-fabricated to include a plurality of cuts. The cuts are arranged to form a cut pattern which beneficially provides for effective shapeability near the distal tip of the guidewire device 200 while also maintaining good torquability. For clarity, the cut pattern is not shown in FIGS. 10 and 11. Examples of cut patterns which may be utilized in the tube 204 are shown in FIGS. 12 through 14.

The proximal section 210 of the guidewire device 200 extends proximally to a length necessary to provide sufficient guidewire length for delivery to a targeted anatomical area. The proximal section 210 typically has a length ranging from about 50 to 350 cm. The proximal section 210 may have a diameter of about 0.014 inches, or a diameter within a range of about 0.008 to 0.125 inches. The distal section 212 of the core 202 may taper to a diameter of about 0.002 inches, or a diameter within a range of about 0.001 to 0.050 inches. In some embodiments, the tube 204 has a length within a range of about 3 to 100 cm.

In some embodiments, the distal section 212 of the core 202 tapers to a round cross-section. In other embodiments, the distal section 212 of the core 202 has a flat or rectangular cross-section. The distal section 212 may also have another cross-sectional shape, such as another polygon shape, an ovoid shape, an erratic shape, or combination of different cross-sectional shapes at different areas along its length.

Typically, a user will shape the distal end of the guidewire device 200 by manually bending, twisting, or otherwise manipulating the distal 1 cm to 3 cm (approximately) of the guidewire device 200 to a desired shape. This length is shown schematically as the distal "tip" 206 in FIG. 10. In some embodiments, the tip 206 includes one or more shapeable components (within the tube 204) formed from stainless steel, platinum, and/or other shapeable materials. In preferred embodiments, the tip 206 includes one or more components formed from a material that exhibits work hardening properties, such that the tip, when shaped (i.e., plastically deformed), provides a higher elastic modulus at the shaped sections than prior to being shaped.

Figure 11:
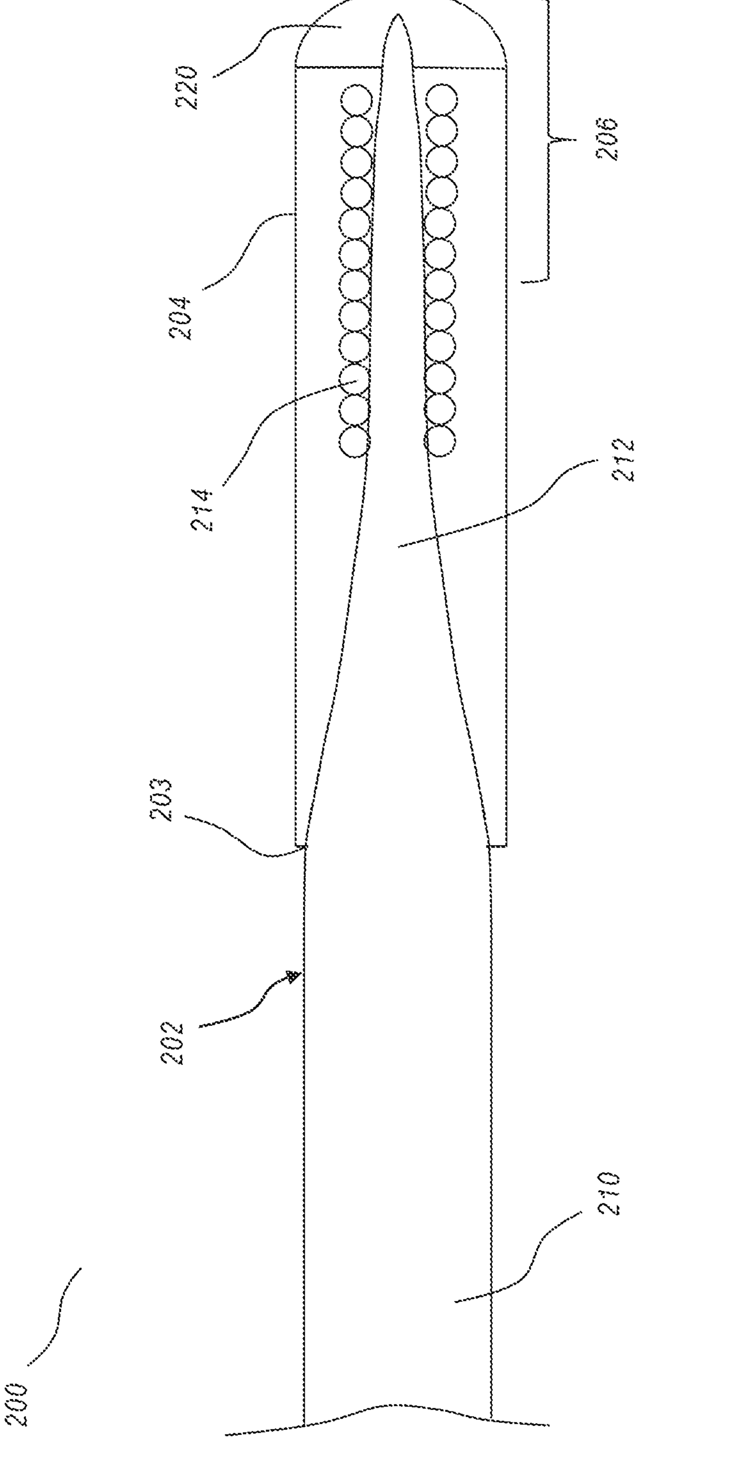
FIG. 11 is a cross-sectional view of the guidewire device of FIG. 10.

FIG. 11 illustrates a cross-sectional view of the guidewire device 200 of FIG. 10. As shown, the core 202 includes a proximal section 210 and a distal section 212, with the distal section having a smaller diameter than the proximal section 210. A coil 214 is positioned upon at least a portion of the distal section 212 of the core 202. The coil 214 is preferably formed from one or more radiopaque materials, such as platinum group, gold, silver, palladium, iridium, osmium, tantalum, tungsten, bismuth, dysprosium, gadolinium, and the like. Additionally, or alternatively, the coil 214 may be at least partially formed from a stainless steel or other material capable of effectively holding shaped after being bent or otherwise manipulated by a user. In the illustrated embodiment, the coil 214 is disposed at or near the distal end of the device and extends a distance proximally toward the attachment point 203. In some embodiments, the coil 214 has a length that substantially coincides with the length of the tube 204. In other embodiments, the coil 214 is shorter. For example, the coil 214 may extend from the distal end by 1, 2, 4, 6, 8, 10, 12, 15, 20, 25, 30, or 35 cm, or may extend from the proximal end a distance within a range defined by any two of the foregoing values.

In some embodiments, the coil 214 is formed as one integral piece. In other embodiments, the coil 214 includes a plurality of separate sections positioned adjacent to one another and/or interlocked through intertwining coils. Such separate segments may additionally or alternatively be soldered, adhered, or otherwise fastened to one another to form the complete coil 214. Some embodiments may include two or more coils, where at least one of the coils is configured to provide radiopacity and at least one of the coils is configured in size and shape to improve centering of the distal section 212 of the core 202 inside the tube 204.

Although the illustrated embodiment shows a space between the coil 214 and the tube 204, it will be understood that this is done schematically for ease of visualization. In some embodiments, the coil 214 is sized to fill and pack a greater proportion of the space between the distal section 212 and the tube 204. For example, the coil 214 may be sized so as to abut both the distal section 212 of the core 202 and the inner surface of the tube 204. Other embodiments include a space between the core 202 and the tube 204 for at least a portion of the section of the guidewire device 200 where the tube 204 and the core 202 are co-extensive.

The coil 214 may beneficially function to pack the space between the core 202 and the tube 204 so as to align the curvature of the distal section 212 of the core 202 with the curvature of the tube 204. For example, when a curvature is formed in the tube 204, the closely packed segments of the coil 214 functions as a packing between the tube 204 and the distal section 212 to impart the same curvature to the distal section 212. In contrast, a guidewire device omitting a coil, when curved at the tube, would not follow the same curve as the tube but would extend until abutting against the inner surface of the tube before being forced to curve.

Embodiments described herein beneficially allow the distal tip 206 to be shaped to a desired position and to remain in the shaped position for a sufficiently extended period of time. In contrast to a conventional guidewire device, the illustrated embodiments are able to form and maintain a shaped configuration. With conventional guidewire devices, problems related to shapeability often occur as a result of a mismatch in properties between the tube structure and the internal components (the core and coil). Tube structures are typically formed from nitinol or other superelastic materials. Such tubes will be, upon being bent or shaped, biased toward their original (straight) position, and will thereby impart recovery forces against any shapeable internal components, resulting in deformation and a loss of the customized shape of the tip.

Often, for example, a conventional guidewire will have a shaped tip prior to deployment, but the shaped tip will be lost or degraded during use of the guidewire as the superelastic tube flexes toward its original shape in opposition to the desired tip shape. The recovery forces imparted by the tube thus act against the internal components to reduce or degrade the desired shape set by the user. In contrast, the embodiments described herein includes features that enable the tip 206 to be shaped without being subjected to overriding recovery forces from the tube. As described below, the tube 204 may include a cut pattern which maintains effective torquability while also providing sufficient flexibility at the distal tip 206 so as to avoid disrupting the custom shape of the tip 206.

FIGS. 12 through 16 illustrate example embodiments of tube cut patterns that may be utilized in one or more of the guidewire device embodiments described herein. For example, the tube 204 of the embodiment shown in FIGS. 10 and 11 may be cut according to one or more of the configurations shown in FIGS. 12 through 16.

FIG. 12 illustrates a tube 504 having a series of cuts 508 which form beams 530 (extending axially) and rings 540 (extending transversely and circumferentially). In the illustrated embodiments, the cuts 508 are arranged on the tube as a series of "bypass cuts." As used herein, a bypass cut is a cut that does not have an opposing cut directly opposite of it with respect to the longitudinal axis of the tube, thereby leaving a single beam 530 of longitudinally extending material between rings 540 of transversely and circumferentially extending material. A "bypass" cut pattern may also be referred to herein as a "one-beam" cut pattern. The transverse cross-sectional geometries of the beams can be a variety of shapes including semi-circular such as those made from a cutting saw with a circular blade, flat sided such as those made from a laser machining operation, or any type of cross sectional shape. In the illustrated embodiment, the cuts are arranged as alternating cuts that are offset by about 180 degrees from one cut to the next along the length of the tube 504, but rotational offsets can also be made at angles that are different than 180 degrees to 0 degrees as described below.

Tubes formed using one or more sections of bypass (i.e., one-beam) cuts as shown can provide a number of benefits, particularly with respect to an associated shapeable tip of a guidewire device. For example, the flexibility of a tube having bypass cuts is relatively greater than the flexibility of a tube having no cuts or having cuts which leave multiple beams between successive rings (e.g., assuming beam width, ring size, and cut spacing is otherwise equal). Beneficially, the increased flexibility provided by the bypass cut arrangement minimizes or prevents the tube from deforming the shape of the internal structures of the guidewire. For example, a core (e.g. stainless steel) disposed within a tube may be bent or curved (i.e., plastically deformed) so as to provide the tip of the guidewire with a desired shape.

As explained above, in many instances, forces associated with elastic recovery of the tube will be imparted against the shaped core and will tend to straighten out the shaped core, at least with respect to the portions of the shaped core that are disposed within the tube. Appropriately tuning the flexibility of the tube therefore reduces the recovery force imparted against the shaped core and allows the shaped core to better maintain its shape.

In some embodiments, the depth of successive bypass cuts or sets of bypass cuts is progressively increased for each successive cut or sets of cuts moving toward the distal end. A cut depth profile can therefore be utilized to configure a tube with the desired flexibility and torquability characteristics for a given application. For example, one tube configuration can include a proximal section with relatively lower flexibility and relatively higher torquability that rapidly progresses to a distal section with relatively higher flexibility and relatively lower torquability as bypass cuts rapidly get progressively deeper toward the distal end. In some embodiments, the section having relatively deeper cuts is formed only at the distal-most section of the tube where shapeability is expected or desired (e.g., the distal 1 to 3 cm of the tube), so as to preserve higher torquability for the remainder of the tube.

Bypass cuts 508 may be varied according to depth, width, and/or spacing. For example, cuts 508 may get progressively deeper and/or more closely spaced the closer they get to the distal tip of the device. Cuts that are deeper and/or more closely spaced provide relatively greater flexibility. Thus, a gradient may be formed which provides for increasing guidewire flexibility at progressively more distal regions of the guidewire. As described in more detail below, bypass cuts 508 may also be arranged with alternating angular positions according to an angular offset applied at each adjacent cut or applied at adjacent sets of cuts. The illustrated embodiment shows an angular offset of 180 degrees from one cut to the next. Some embodiments may include an angular offset of about 5, 15, 30, 45, 60, 75, 80, or 85 degrees from one cut to the next or from one set of cuts to the next set of cuts.

FIG. 13 illustrates another embodiment of a tube 604 having bypass cuts and a set of opposing, depth-offset two-beam cuts disposed proximal to the bypass cuts. In the illustrated embodiment, a set of bypass cuts results in the beams 630. Proximal to the beams 630 is a set of cuts arranged as opposing cuts which result in beams 634. Although not visible in this view, an additional beam is formed opposite each beam 634 (hidden behind beams 634 in this view). Each ring 640 within the depth-offset two-beam cut pattern therefore has a set of two beams connecting it to its proximally adjacent ring, and a set of two beams connecting it to its distally adjacent ring.

As shown, the opposing two-beam cuts are offset in depth so that, for each opposing cut pair (one cut on each side of the tube axis), one of the cuts has a depth that is greater than the opposite cut. Such depth-offset two-beam cuts may be advantageously used to transition from a length of bypass cuts (such as shown in FIG. 12) to a length of non-offset opposing two-beam cuts (such as shown in FIG. 14).

FIG. 14 illustrates a section of tube 250 having a two-beam cut pattern, with each cut of each opposing cut pair having approximately the same cut depth so that the resulting beams are substantially equally circumferentially spaced. As shown, the cuts result in a pair of beams 234 formed between each of the rings 240. The cuts are shown here as being angularly offset by about 90 degrees from one pair of opposing cuts to the next, though other angular offsets may be utilized.

A section of tube having a two-beam cut pattern with substantially circumferentially equally spaced beams will typically have relatively higher ability to transmit torque and relatively lower flexibility, while a section of tube having bypass cuts will typically have relatively lower ability to transmit torque and relatively higher flexibility. A section of tube having a depth-offset two-beam cut configuration will typically have a torque transmissibility and flexibility between that of a section of depth-symmetric opposing two-beam cuts and a section of bypass cuts. The greater the difference between the depths of opposing cuts, the closer together circumferentially the resulting beams will be, and therefore the more similar the offset two-beam cut will be to a one-beam/bypass cut. Likewise, the more similar the depths of the opposing cuts are, the more similar the offset two-beam cut will be to a symmetric two-beam cut.

Embodiments of tubes including an offset two-beam section advantageously provide a transition zone that may be positioned and configured to provide desired transition properties between a distal bypass cut zone and a proximal symmetric two-beam section. For example, the transition zone may be relatively gradual or abrupt, depending on the length of the transition zone and/or depending on the rapidity of change to the offset in successive cuts. Tubes may therefore be configured to provide a proximal section with greater torquability and less flexibility, which transition to a more flexible distal section with greater flexibility to better maintain a bent shape when shaped by an operator. The positions and configurations of the proximal section, transition section, and distal section are tunable to optimize the benefits of effective torquability and shapeable tip performance.

Figure 15:
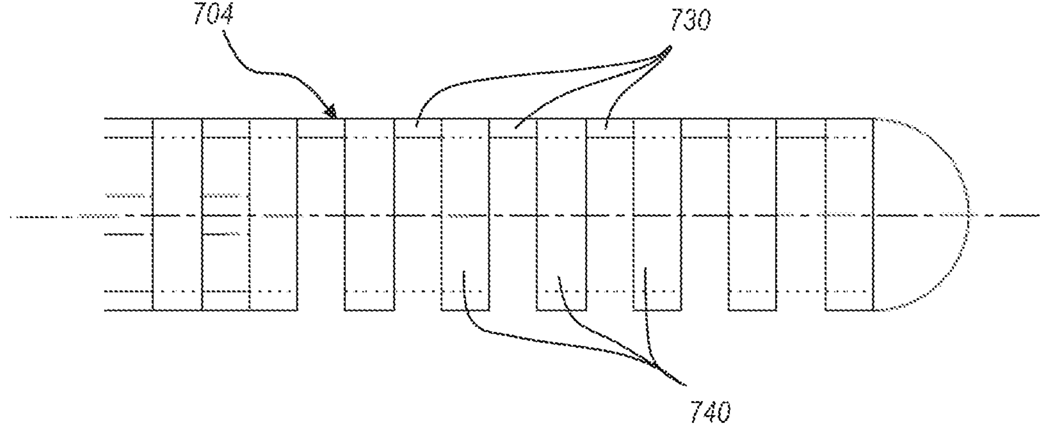
FIG. 15 illustrates an embodiment of a tube structure including a section having a one-sided one-beam cut pattern.

FIG. 15 illustrates another embodiment of a tube 704 having one-beam cuts forming a plurality of beams 730 and rings 740. As shown, the cuts are arranged so that the beams 730 are aligned along one side of the tube 704, rather than being alternatingly positioned by 180 degrees or some other angular amount. Such an embodiment can beneficially provide preferential bending in one direction (e.g., toward the aligned beams 730) so that the associated recovery force back toward the axis of the tube is further minimized.

Figure 16:
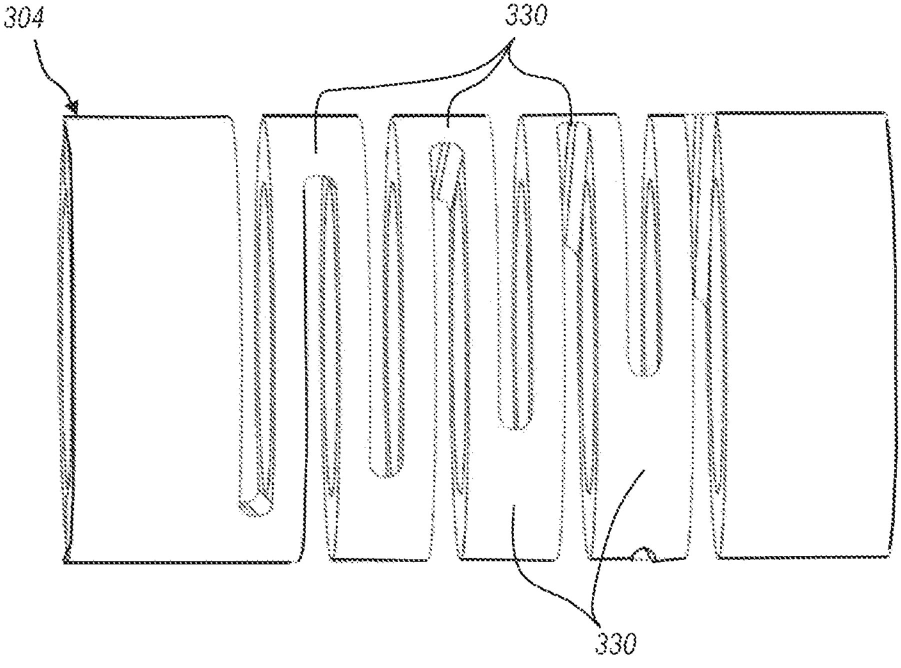
FIG. 16 illustrates an embodiment of a tube structure including a bypass cut pattern with an example angular offset providing a helical pattern of resulting beams.

FIG. 16 illustrates an embodiment of a tube 304 having a bypass cut pattern and an angular offset between sets of cuts. As shown, the angular offset positions resulting beams 330 in a rotating/helical circumferential pattern along the length of the tube section. In some embodiments, a first angular offset is applied from one cut to the next within a set of cuts, and a second angular offset is applied from one set of cuts to the next set of cuts. For example, as illustrated in FIG. 16, each cut 308 in a pair of adjacent cuts may be offset by about 180 degrees so as to leave resultant beams 330 on opposite sides of one another with respect to the longitudinal axis of the guidewire, while each pair is offset from an adjacent pair by some other angular offset (e.g., by about 5 degrees in the illustrated embodiment). In this manner, the intra-set angular offset can position beams 330 on opposite sides of the guidewire axis, while the inter-set angular offset can adjust the angular position of successive beams enough to minimize preferred bending directions of the guidewire over a length of several sets of cuts 308.

Rotational offsets may also be applied to the cut patterns illustrated in FIGS. 12 through 15. In preferred embodiments, each successive cut or sets of cuts (e.g., every second cut, third, fourth, etc.) along the length of a given section is rotationally offset by about 1, 2, 3, 5, or 10 degrees, or is offset by about 1, 2, 3, 5, or 10 degrees off from 90 degrees in a two-beam configuration or 1, 2, 3, 5, or 10 degrees off from 180 degrees in a one-beam configuration. These rotational offset values have beneficially shown good ability to eliminate flexing bias.

For example, in a two-beam cutting pattern where each pair of beams are equally circumferentially spaced such as shown in FIG. 14, a rotational offset that is about 1, 2, 3, 5, or 10 degrees off from 90 degrees positions every other pair of beams along the length of the cut section with a misalignment of a few degrees. For example, a second pair of beams may be rotationally offset from a first pair of beams by slightly more or less than 90 degrees, but a third pair of beams will only be rotationally offset from the first pair by a few degrees, and a fourth pair of beams will only be rotationally offset from the second pair by a few degrees. When several successive pairs of beams are arranged this way along the length of a cut section of the guidewire device, the resulting structure allows the cut pattern to enhance flexibility without introducing or aggravating any directional flexibility bias.

The separate components and features of the tube embodiments shown in FIGS. 12 through 16 may be combined to form different tube configurations. For example, some tubes may be configured so as to have a section of bypass (one-beam) cuts (as in FIGS. 12, 15, and/or 16) and a section of symmetrically spaced two-beam cuts (as in FIG. 14), optionally also having one or more depth-offset two-beam cuts (as in FIG. 13). For example, some tube embodiments may include a proximal section having a symmetrically spaced two-beam cut pattern which transitions to a distal section having a bypass cut arrangement.

The embodiments described herein can beneficially enable more proximal regions of the tube to transmit relatively more torque, while reducing the torquability of more distal sections of the tube to allow for tip shaping without overly sacrificing torquability. Accordingly, the features of a guidewire device may be tuned to a particular need or application to optimize the operational relationship between torquability, flexibility, and tip shapeability.

In preferred embodiments, the shapeable distal section of the core has a stiffness that is able to withstand an expected bending force from the tube acting upon the distal section of the core after it has been shaped. In some embodiments, the shapeable distal section of the core is formed from a material or combination of materials providing a modulus of elasticity that is about 1.5 to 4 times greater, or about 2 to 3 times greater than the modulus of elasticity of the material(s) used to form the tube.

Figure 17:
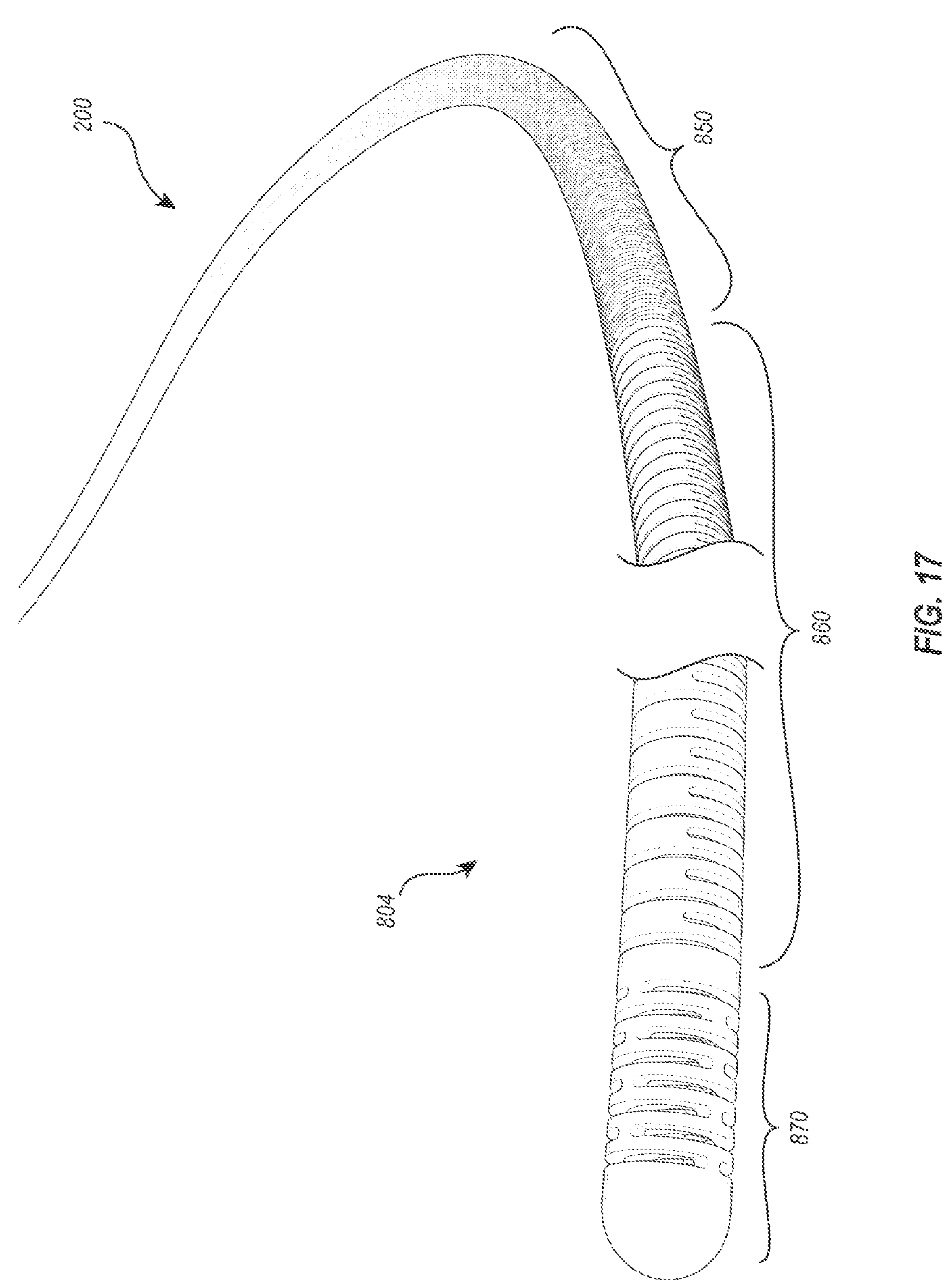
FIG. 17 illustrates a perspective view of an embodiment of a tube structure including three sections.

FIG. 17 illustrates an embodiment of a tube 804 having a first section 850, a second section 860, and a third section 870. The second section 860 is distal to the first section 850 and the third section 870 is distal to the second section 860. Each of the sections 850, 860, 870 may be distinguished from one another by the cutting pattern of each section. As discussed above with reference to other embodiments described herein, the cutting pattern may produce rings 840 and beams 803 within the tube. The sections 850, 860, 870 illustrated in FIG. 17 may have different cutting patterns in each section. For example, the first section 850 may have a two-beam cutting pattern, the second section 860 may have a one-beam cutting pattern, and the third section 870 may have a two-beam cutting pattern.

One will appreciate that other embodiments may include different cutting patterns from those illustrated in FIG. 17. For example, in one embodiment, the first section 850 may have a cutting pattern of greater than two beams, the second section 860 may have a two-beam cutting pattern or one-beam cutting pattern, and the third section 870 may have a one-beam cutting pattern or may be omitted. Also, other embodiments of the tube 804 may include more or less than three sections along the length thereof. For example, one embodiment of the tube 804 may include four or more sections. Also, for example, one embodiment of the tube 804 may include only one or two sections. Cut patterns shown in any of the other embodiments described herein may be utilized.

Figure 18A:
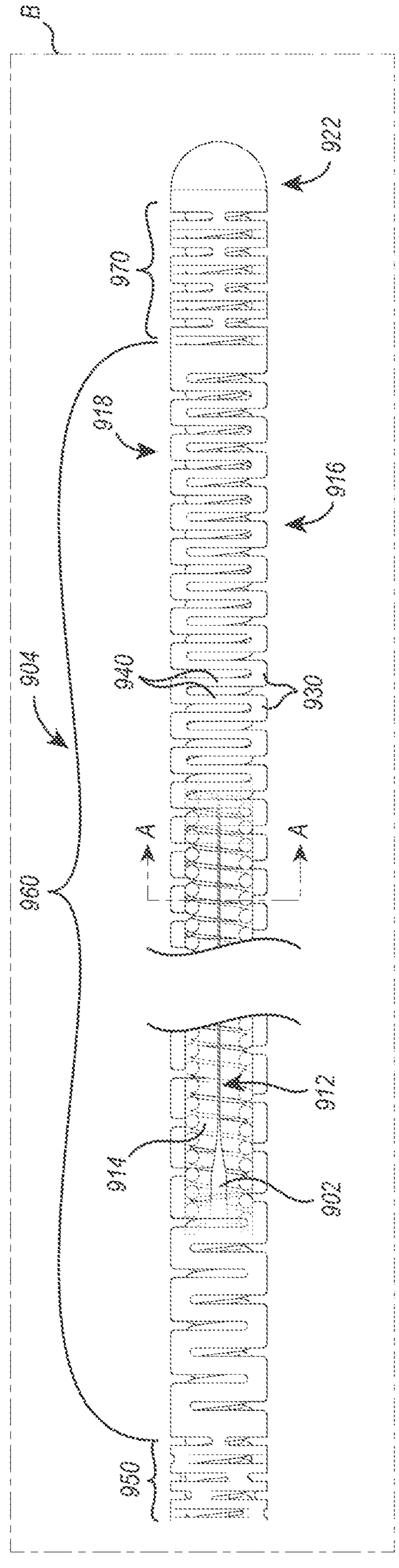
FIG. 18A illustrates a side view of an embodiment of a tube including a distal section of a core disposed therein.

FIG. 18A illustrates a side view of an embodiment of a tube 904 similar to the embodiment of the tube illustrated in FIG. 17. The tube of FIG. 18A also shows a partial cross-sectional view of the second section 960 to illustrate a distal section 912 of the core 902 extending through the tube 904 and the coil 914. Although only a partial cross-section is shown here, it will be understood that the core 902 will typically extend all the way to the distal end 922 of the device. In the illustrated embodiment, the second section 960 of the tube 904 includes a one-beam cutting pattern. The one-beam cutting pattern creates a series of axially extending beams 930 each disposed between a pair of adjacent circumferentially extending rings 940.

In the illustrated embodiment, successive beams 930 alternate in position from a first side 916 of the tube 904 to a second side 918 of the tube 904 (i.e., each successive beam 930 has a rotational offset of about 180°). In another embodiment, the beams 903 of the one-beam cutting pattern of the second section 960 may all be positioned along the same side of the tube to form a backbone of aligned beams 930 extending axially along the tube 904 and connecting the plurality of rings 940, similar to the embodiment shown in FIG. 15.

The one-beam cutting pattern of the second section 960, shown in FIG. 18A, forms a preferred bending plane B. The preferred bending plane B extends axially along the tube 904 and transversely across the tube 904, as indicated in FIG. 18A. Because the beams 930 of the second section 960 extend axially with the tube 904, the tube 904 is most flexible along the preferred bending plane B. That is, the beams 930 are configured such that the tube 904 is least resistant to being bent along the preferred bending plane B compared to any other planes. In this example embodiment, the cutting pattern of the second section 960, whether producing an alternating pattern of beams 930 as shown in FIG. 18A or the single backbone of beams 930 as discussed above, produces a preferred bending plane B.

Figure 18B:
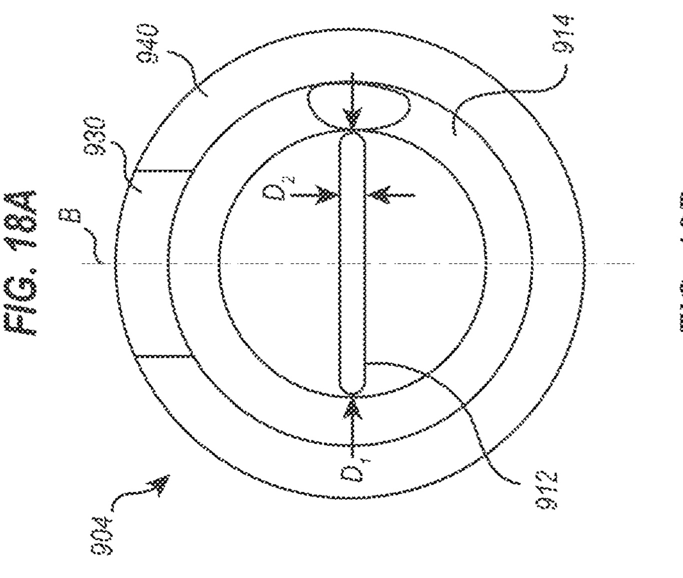
FIG. 18B illustrates a cross-sectional view of the tube of FIG. 18A.

Also, as shown in FIG. 18A, the distal section 912 of the core 902 tapers as it extends distally through the coil 914 and tube 904 and tapers at the distal portion into a flat, ribbon-like configuration. FIG. 18B illustrates a transverse cross-sectional view of the tube 904 through plane A-A of FIG. 18A. The distal section 912 of the core 902 is a substantially flat ribbon extending axially within at least the second section 960 of the tube 904. The ribbon configuration of the core 912 has a major dimension D1 and a minor dimension D2. The major dimension D1 of the distal section 912 of the core 902 is larger than the minor dimension D2 of the core 912 so that a major plane of the ribbon-like distal section 912 of the core 902 extends orthogonally (and preferably perpendicularly) to the preferred bending plane B. In this way, the distal section 912 of the core 902 is also least resistant to bending within the preferred bending plane B, along with the tube 904. In other words, the core 912 may taper to a ribbon-like configuration and extend axially along the tube 904 such that the distal section 912 of the core 902 is aligned with the beams 930 of the second section 960 so that it shares the preferred bending plane B with the tube 904.

In one embodiment, the second section 960 of the tube 904 is about 0.5 cm to about 5 cm in length. In another embodiment, the second section 960 of the tube 904 is about 1 cm to about 2 cm in length. In yet another embodiment, the second section 960 of the tube 904 is about 1 cm to about 1.5 cm in length. The distance from the distal end 922 to which the second section 960 extends may vary depending on the length of the tube 904 that is bent or shaped for a given procedure. These distances may vary between embodiments to accommodate various procedures, as necessary. Other features of the embodiments illustrated in FIGS. 17 through 18B, including materials and dimensions of the coil 914, tube 904, and core 902, and including particular features relating to the cutting patterns, may be similar to other embodiments described herein with reference to the other figures.

Figure 19:
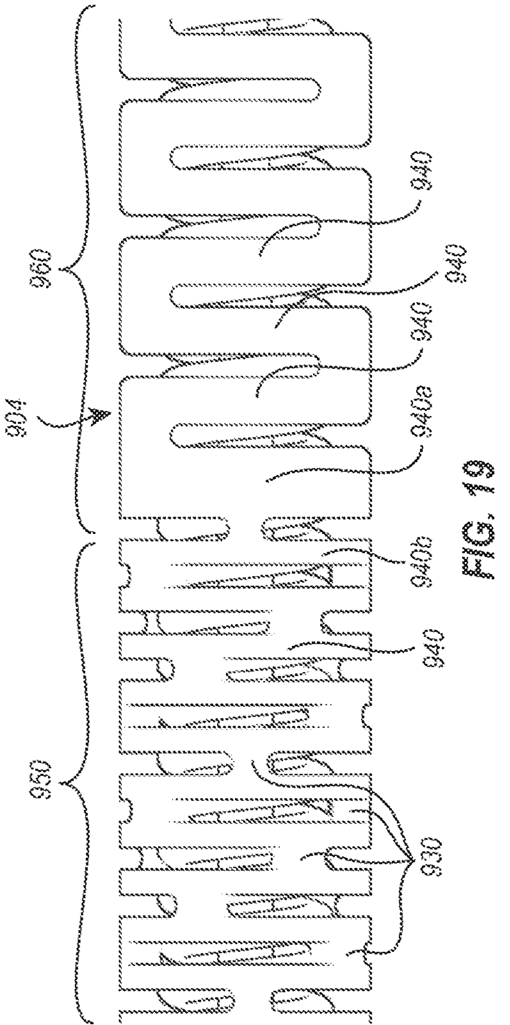
FIG. 19 illustrates an expanded side view of a transition between the first section and the second section of the tube of FIGS. 18A and 18B.

FIG. 19 illustrates a close-up view of a transition between the first section 950 and the second section 960 of the tube 904. In the illustrated embodiment, the first section 950 includes a two-beam cutting pattern and the second section 960 includes a one-beam cutting pattern. The stiffness of the tube 904 in each section depends, at least in part, on the amount of material remaining in the tube 904 once the cuts have been made and in the arrangement/spacing of the remaining beams 930. For example, a section of the tube 904 having two beams 930 between each pair of adjacent rings 940 will, all else being equal, have a greater stiffness than a section of the tube 904 having a single beam 930 of the same size between each pair of adjacent rings 940. Also, for example, a section of the tube 904 having a greater distance between cuts will, all else being equal, have a greater stiffness than a section with less distance between cuts. That is, the greater the distance between the cuts, the greater the thickness of the rings 940 formed between the cuts, and the greater the stiffness of the tube 904 in that section.

The cuts, rings 940, and beams 930 disposed at or near the transition point between the first section 950 and the second section 960 of the tube 904 illustrated in FIG. 19 are configured such that the stiffness profile of the tube 904 is approximately continuous across the transition between the two sections 950 and 960. In other words, the cutting patterns of the first and second sections 950 and 960 are arranged to avoid a significant jump up or down in stiffness from one side of the transition point to the other.

Of course, some level of discrete change in stiffness from measured segment to measured segment may be present depending on the particular level of granularity at which the stiffness is measured along the tube 904 and depending on the specified length of the measured segments. Because an infinite number of stiffness measurements cannot be made, a practically measurable stiffness profile will consist of measured stiffness levels at each of a series of discrete segment lengths of the tube. While jumps (i.e., change in stiffness) from one measured segment to the next measured segment may be discrete, the overall pattern of such jumps preferably approximates a linear series or at least a smooth curve. Thus, in the context of this disclosure, a "significant jump" occurs where a jump from one segment to the next is greater than either immediately adjacent jump by a factor of more than about 1.5. A significant jump is therefore avoided and the stiffness profile across the transition point is therefore "continuous" when no jump across the transition point is greater than either adjacent jump by a factor of more than about 1.5. Preferably no jump across the transition point is greater than either adjacent jump by a factor of more than about 1.2.

FIG. 19 illustrates an embodiment of the tube 904 having rings 940 and beams 930 that accomplish a continuous stiffness profile across the transition between sections 950, 960. In the illustrated embodiment, the axial thickness of the most proximal ring 940*a* of the second section 960 is greater than the axial thickness of the most distal ring 940*b* of the first section 950. In this way, the total amount of material of the tube 904 at the transition is similar between the sections 950, 960 at or near the transition. This results in a continuous stiffness across the transition, as described above. In addition, the axial thickness of the rings 940 of the second section 960 may decrease distally along the length of the tube 904 so that the stiffness correspondingly decreases. This is illustrated in FIG. 19 but shown more dramatically in FIG. 18A.

Figure 20:
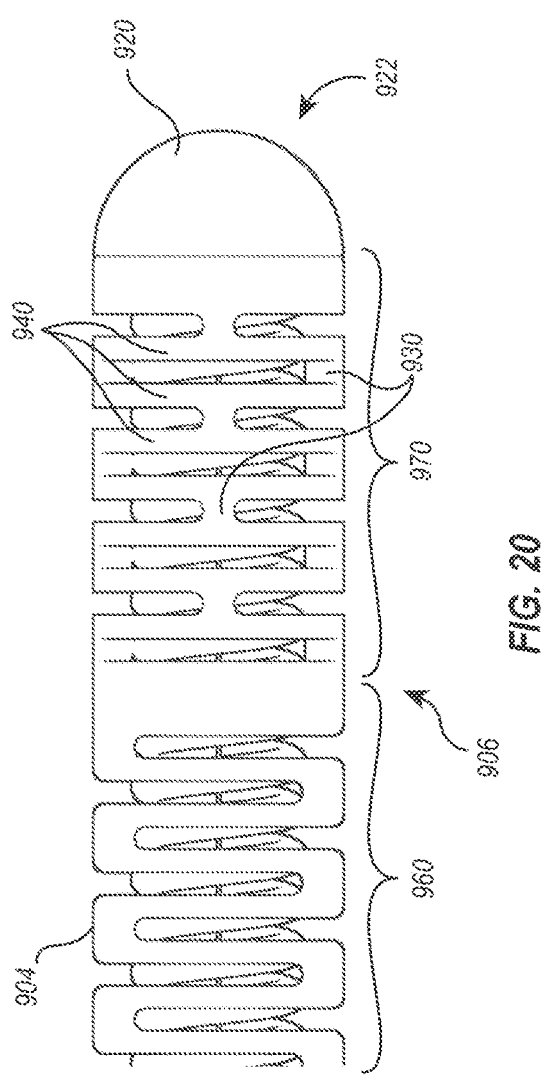
FIG. 20 illustrates an expanded side view of the distal tip of the tube of FIGS. 18A and 18B, including the second and third sections thereof.

Turning now to FIG. 20, the distal tip 906 of the tube 904 is shown. The distal tip 906 shown in FIG. 20 includes the third section 970, at least a portion of the second section 960, and a polymer adhesive 920 disposed distal to the third section 970 at the distal end 922 of the tube 904. The third section 970 of the tube 904 includes a two-beam cutting pattern forming two beams 930 between each pair of adjacent rings 940. This contrasts with the one-beam cutting pattern of the second section 960. One will appreciate that a transition between the second section 960 and the third section 970 may be similar to the transition between the first section 950 and the second section 960, as described above. That is, the stiffness of the tube 904 may be approximately continuous across the transition from the second section 960 to the third section 970.

The adhesive 920 disposed at the distal end 922 of the tube 904 may extend between the tube 904 and the core at the distal end 922 of the tube 904 to secure the tube 904 and core together. As illustrated in FIG. 10, the distal section 212 of the core 202 may extend distally beyond the tube 204 and into the adhesive 220. The adhesive 220 can thus function to couple the tube 204 to the core and/or coil 214.

Referring again to FIG. 20, the adhesive 920 may be disposed on the distal end 922 of the tube 904 and at least partially wick proximally and into one or more of the cuts between the various rings 940 and beams 930 of the third section 970. The two-beam cutting pattern of the third section 970 provides added surface area of the tube 904 material, compared to the one-beam cutting pattern of the second section 960, to which the adhesive 920 can bond. Thus, the two-beam cutting pattern of the third section 970 provides a stronger coupling between the adhesive 920 and distal section of the core and/or coil. One will appreciate that cutting patterns including more than two beams 930 between each pair of adjacent rings 940 may therefore serve to enhance the strength of the coupling between the tube 904 and the distal section of the core 202 and/or the coil. However, as discussed above, the more material the cuts remove from the tube 904, the less stiff the tube 904 will be, and vice versa.

Also, during manufacturing, disposing a larger amount of adhesive 920 on the distal end 922 of the tube 904 will result in the adhesive 920 wicking further proximally up the tube 904. The two-beam cutting pattern of the third section 970 provides an effective visual indicator to a manufacturer, due to the number and spacing of the cuts in the cutting pattern, in order to see how far proximally up the third section 970 the adhesive 920 wicks. This visual indication of the third section 970 may also assist a machine or other automated manufacturing device in detecting how far the adhesive 220 wicks proximally up the third section 970 during manufacturing.

For example, when a manufacturer disposes the adhesive 920 on the distal end 922 of the tube 904 during manufacturing, the adhesive may begin to wick through the spaces between the rings 940 and beams 930 in the third section 970. Because the two-beam cutting pattern of the third section 970 provides a visual indicator, in contrast to the one-beam cutting pattern of the second section 960, the manufacturer can more easily discern how far proximally up the tube 904 the adhesive wicks from one ring 940 to the next. The manufacturer can therefore determine how much adhesive 220 to dispose onto the distal end 922 of the tube 904. The manufacturer can also determine when to stop adding adhesive 220 based on a predetermined distance or ring 940 to which the adhesive 920 has wicked.

In one embodiment, the third section 970 of the tube 904 extends between about 0.5 mm and 1.5 mm from distal a distal end 922 of the tube 904. In another embodiment, the third section 970 of the tube 904 extends between about 0.75 mm and 1.25 mm from distal a distal end 922 of the tube 904. In yet another embodiment, the third section 970 of the tube 904 extends about 1 mm from distal a distal end 922 of the tube 904. The distance from the distal end 922 to which the third section 970 extends may vary depending on the length of the tube 904 that is needed to be bent or shaped, or the distance necessary for the adhesive 920 to wick sufficiently up the tube 904. These distances may vary between embodiments to accommodate various tubes and procedures, as necessary. Other features of the embodiments illustrated in FIGS. 19 and 20, including materials, properties, and dimensions of the coil 914, tube 904, and core 902, may be similar to other embodiments described herein with reference to the other figures.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

As used herein, the term "microfabricated" refers to any fabrication process capable of manipulating a stock material to form a catheter device having one or more of the features disclosed herein, including any fabrication process capable of forming gaps in an inner shaft as disclosed herein. Examples include, but are not limited to, laser cutting and blade cutting.

For any given element of component of a described embodiment, any of the possible alternatives listed for that element or component may generally be used individually or in combination with one another, unless implicitly or explicitly stated otherwise.

Unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. An intravascular system, comprising:

a catheter device:

wherein the catheter device is configured for navigation through a vessel that comprises one or more curves with a radius of curvature of 10 mm or less, wherein a ratio of an inner diameter of the vessel to an outer diameter of the catheter device, for at least a portion of the vessel, is about 300% to about 800%;

wherein the catheter device comprises an inner shaft that includes a plurality of gaps formed in the inner shaft the inner shaft including a bending stiffness profile with a bending stiffness slope defined by a change in bending stiffness over a length of the catheter device;

wherein the catheter device comprises an outer member that includes a transition section where a first polymer transitions to a second polymer of different hardness; and wherein the inner shaft comprises a length that crosses the transition section, and wherein a size and/or spacing of the plurality of gaps are configured so that the bending stiffness slope of the inner shaft at the length that crosses the transition section is less steep than the bending stiffness slopes proximal and distal of the length that crosses the transition section; and a guidewire device configured for navigation through the vessel, wherein the catheter device and the guidewire device are configured to enable the catheter device to advance over the guidewire device in response to a push force of 50 g or less applied to the catheter device.

2. The intravascular system of claim 1, wherein a path length of the vessel through which the catheter device is configured to navigate is at least 10 cm.

3. The intravascular system of claim 1, wherein a path length of the vessel through which the catheter device is configured to navigate is at least 20 cm.

4. The intravascular system of claim 1, wherein the one or more curves comprise 3 or more curves.

5. The intravascular system of claim 1, wherein the one or more curves each have a radius within a range of about 4 mm to about 9 mm.

6. The intravascular system of claim 1, wherein the catheter device is configured to advance over the guidewire device in response to a push force of 40 g or less applied to the catheter device.

7. The intravascular system of claim 6, wherein the catheter device is configured to advance over the guidewire device in response to a push force of 30 g or less applied to the catheter device.

8. The intravascular system of claim 7, wherein the catheter device is configured to advance over the guidewire device in response to a push force of 20 g or less applied to the catheter device.

9. The intravascular system of claim 1, wherein the ratio of the inner diameter of the vessel to the outer diameter of the catheter device is at least about 371%.

10. The intravascular system of claim 1, wherein the inner shaft includes a plurality of axially extending beams that couple a plurality of circumferentially extending rings.

11. The intravascular system of claim 10, wherein the inner shaft includes a three-beam section and a two-beam section, wherein the three-beam section is disposed proximal of the two-beam section, and wherein at least a portion of the three-beam section has a higher bending stiffness than the two-beam section.

12. The intravascular system of claim 1, wherein the second polymer is proximal of the first polymer and has a greater hardness than the first polymer such that the outer member increases in bending stiffness across the transition section in the distal to proximal direction.

13. The intravascular system of claim 1, further comprising an inner liner around which the inner shaft is positioned.

14. The intravascular system of claim 13, wherein the first polymer and the second polymer of the outer member is fused to the inner liner, fills the plurality of gaps of the inner shaft, and covers outer surfaces of the inner shaft to encapsulate and embed the inner shaft.

15. The intravascular system of claim 1, wherein the inner shaft is formed from nitinol.

16. The intravascular system of claim 1, wherein the catheter device has a bending stiffness slope ((N·m2)/cm)) of no more than about $6.0\times10^{-7}$ for a distal 15 cm section, no more than about $9.0\times10^{-7}$ for a distal 35 cm section, and/or no more than about $9.0\times10^{-7}$ for a distal 50 cm section.

17. The intravascular system of claim 1, wherein the guidewire device comprises:

a core having a proximal section and a distal section; and a tube structure coupled to the core such that the distal section of the core passes into the tube structure, the tube structure having a first section and a second section distal to the first section, wherein the tube structure includes a cut pattern which forms a plurality of axially extending beams coupling a plurality of circumferentially extending rings.

18. The intravascular system of claim 17, wherein the plurality of axially extending beams extend parallel to a longitudinal axis of the tube structure.

19. The intravascular system of claim 17, wherein the plurality of circumferentially extending rings form fully enclosed rings.

* * * * *